(12) United States Patent
Sonomoto et al.

(10) Patent No.: US 9,234,219 B2
(45) Date of Patent: Jan. 12, 2016

(54) METHOD FOR PRODUCING L-LACTIC ACID BY LACTIC ACID BACTERIUM UNDER PRESENCE OF PENTOSE AND CELLOOLIGOSACCHARIDES

(75) Inventors: Kenji Sonomoto, Fukuoka (JP); Takeshi Zendo, Fukuoka (JP)

(73) Assignees: KYUSHU UNIVERSITY, NATIONAL UNIVERSITY CORPORATION, Fukuoka-Shi (JP); SUMITOMO CORPORATION, Tokyo (JP)

( * ) Notice: Subject to any disclaimer, the term of this patent is extended or adjusted under 35 U.S.C. 154(b) by 0 days.

(21) Appl. No.: 13/810,426

(22) PCT Filed: Jul. 15, 2011

(86) PCT No.: PCT/JP2011/066260
§ 371 (c)(1),
(2), (4) Date: Mar. 28, 2013

(87) PCT Pub. No.: WO2012/008589
PCT Pub. Date: Jan. 19, 2012

(65) Prior Publication Data
US 2013/0203134 A1 Aug. 8, 2013

(30) Foreign Application Priority Data

Jul. 16, 2010 (JP) .................................. 2010-162227
Feb. 2, 2011 (JP) .................................. 2011-020593

(51) Int. Cl.
*C12P 7/56* (2006.01)
*C12P 7/62* (2006.01)
*C12R 1/46* (2006.01)
*C12N 1/20* (2006.01)

(52) U.S. Cl.
CPC ... *C12P 7/56* (2013.01); *C12N 1/20* (2013.01); *C12P 7/625* (2013.01); *C12R 1/46* (2013.01)

(58) Field of Classification Search
None
See application file for complete search history.

(56) References Cited

U.S. PATENT DOCUMENTS

2013/0203134 A1    8/2013    Sonomoto et al.

FOREIGN PATENT DOCUMENTS

| JP | 9-135681 A | 5/1997 |
| JP | 9-173090 A | 7/1997 |
| JP | 2002-186938 A | 7/2002 |
| JP | 2003-164276 A | 6/2003 |
| JP | 2003-235529 A | 8/2003 |
| JP | 2006-42796 A | 2/2006 |
| JP | 2009-195251 A | 9/2009 |
| WO | WO 2005/100543 A1 | 10/2005 |
| WO | WO 2012/008585 A1 | 1/2012 |

OTHER PUBLICATIONS

Abdel-Rahman et al., Appl. Microbiol Biotechnol., Published online on Nov. 2010, vol. 89, p. 1039-1049.*
Adsul et al., Green Chem., 2007, vol. 9, p. 58-62 (published online Oct. 2006).*
Zhang et al., Bioresource Technology, 2008, vol. 99, p. 855-862.*
US Office Action issued in U.S. Appl. No. 13/810,411 on Jul. 23, 2014.
Abe et al., "Simultaneous Saccharification and Fermentation of Cellulose to Lactic Acid", Biotechnology and Bioengineering, vol. 37 (1991), pp. 93-96.
Cai, "Identification and Characterization of *enterococcus* Species Isolated from Forage Crops and Their Influence on Silage Fermentation", J. Dairy Sci, vol. 82 (1999), pp. 2466-2471.
International Preliminary Report on Patentability and Translation of the Written Opinion of the International Searching Authority, dated Feb. 12, 2013, for International Application No. PCT/JP2011/066253 (Forms PCT/IB/373 and PCT/ISA/237).
International Preliminary Report on Patentability and Translation of the Written Opinion of the International Searching Authority, dated Feb. 21, 2013, for International Application No. PCT/JP2011/066260 (Forms PCT/IB/338, PCT/IB/373 and PCT/ISA/237).
International Preliminary Report on Patentability and Written Opinion of the International Searching Authority, dated Jan. 22, 2013, for International Application No. PCT/JP2011/066253 (Forms PCT/IB/373 and PCT/ISA/237).
International Preliminary Report on Patentability and Written Opinion of the International Searching Authority, dated Jan. 31, 2013, for International Application No. PCT/JP2011/066260 (Forms PCT/IB/373 and PCT/ISA/237).
International Search Report, dated Aug. 9, 2011, for International Application No. PCT/JP2011/066260.
International Search Report, dated Oct. 18, 2011, for International Applcation No. PCT/JP2011/066253.
Ishikawa et al., "*Halolactibacillus halophilus* gen. nov., sp. nov. and *Halolactibacillus miurensis* sp. nov., halophilic and alkaliphilic marine lactic acid bacteria constituting a phylogenetic lineage in Bacillus rRNA group 1", Intl. Jour. of Systematic and Evolutionary Microbiology, vol. 55 (2005), pp. 2427-2439.
Joshi et al., "Strain improvement of Lactobacillus lactis for D-lactic acid production", Biotechnol Lett, vol. 32 (2010), pp. 517-520.
Ohara et al., "Calculation of Metabolic Flow of Xylose in Lactococcus lactis", Journal of Bioscience and Bioengineering, vol. 103, No. 1 (2007), pp. 92-94.
Ohara et al., "Xylooligosaccharide Fermentation with Leuconostoc lactis", Journal of Bioscience and Bioengineering, vol. 101, No. 5 (2006), pp. 415-420.
Okano et al., "D-lactic acid production from cellooligosaccharides and β-glucan using L-LDH gene-deficient and endoglucanase-secreting Lactobacillus plantarum", Appl. Microbiol Biotechnol, vol. 85 (2010), pp. 643-650.
Oshiro et al., "Kinetic modeling and sensitivity analysis of xylose metabolism in Lactococcus lactis IO-1", Journal of Bioscience and Bioengineering, vol. 108, No. 5 (2009), pp. 376-384.

(Continued)

*Primary Examiner* — Kade Ariani
(74) *Attorney, Agent, or Firm* — Birch, Stewart, Kolasch & Birch, LLP

(57) ABSTRACT

The present invention thus provides a method for producing L-lactic acid, which comprises the step of culturing a lactic acid bacterium that can produce L-lactic acid in a medium containing any one selected from the group consisting of cellobiose, cellooligosaccharides, xylose, arabinose, and glucose derived from cellulose and/or hemicellulose as a substrate to obtain L-lactic acid. In a preferred embodiment of the present invention, *Enterococcus mundtii* NITE BP-965 can be used.

9 Claims, 7 Drawing Sheets

(56) References Cited

OTHER PUBLICATIONS

Romero-Garcia et al., "Homolactic fermentation from glucose and cellobiose using Bacillus subtilis", Microbial Cell Factories, vol. 8, No. 23 (2009), pp. 1-8.

Tanaka et al., "Two different pathways for D-xylose metabolism and the effect of xylose concentration on the yield coefficient of L-lactate in mixed-acid fermentation by the lactic acid bacterium Lactococcus lactis IO-1", Appl Microbiol Biotechnol, vol. 60 (2002), pp. 160-167.

Venkatesh, "Simultaneous Saccharification and Fermentation of Cellulose to Lactic Acid", Bioscience Technology, vol. 62 (1997), pp. 91-98.

Office Action for Japanese Application No. 2012-524617, dated Jun. 18, 2013.

Abdel-Rahman et al., "Special Abstracts", Journal of Biotechnology, Nov. 2010, p. S347, vol. 150, Supplement 1, #P-I.16.

Abdel-Rahman et al., "Special Abstracts", Journal of Biotechnology, Nov. 2010, p. S347-S348, vol. 150, Supplement 1, #P-I.17.

Abdel-Rahman et al., Efficient Homofermentative L-(+)-Lactic Acid Production from Xylose by a Novel Lactic Acid Bacterium, Enterococcus mundtii QU 25, Applied and Environmental Microbiology, Mar. 2011, pp. 1892-1895, Vo. 77, No. 5.

Collins et al., "*Enterococcus mundii*, sp. nov.", International Journal of Systematic Bacteriology, 1986, pp. 8-12, vol. 36, No. 1.

Japanese Office Action dated Aug. 18, 2015 for Japanese Patent Application No. 2013-055145.

\* cited by examiner

METHOD FOR PRODUCING L-LACTIC ACID BY LACTIC ACID BACTERIUM UNDER PRESENCE OF PENTOSE AND CELLOOLIGOSACCHARIDES

TECHNICAL FIELD

The present invention relates to a method for producing L-lactic acid efficiently by lactic acid bacterium under presence of pentose and cellooligosaccharides.

BACKGROUND ART

Polylactic acid (PLA) is expected as a base material for sustainable society in view of not only biodegradability thereof, but also, in these days, the characteristic that it can be produced by using biomass as a raw material.

Lactic acid monomers used as the raw material of polylactic acid are commercially produced by chemical synthesis or microbial fermentation. Although chemical synthesis of lactic acid always provides a racemic mixture, high optical purity L- or D-lactic acid can be produced by microbial fermentation depending on the selected microorganism. Optical purity of the raw material lactic acid greatly influences on the physical characteristics of polylactic acid. Poly-L-lactic acid (PLLA) formed by polymerization of only L-isomers, and poly-D-lactic acid (PDLA) formed by polymerization of only D-isomers have higher crystallinity compared with poly-DL-lactic acid (PDLLA), which is a random polymer of D-lactic acid and L-lactic acid, and also show higher heat resistance. Therefore, production of high optical purity lactic acid by fermentation is considered important.

Biomass raw materials used for various fermentative productions mainly consist of corn and sugarcane, and edible parts (starch, sucrose) of these are used. If non-edible biomass raw materials such as non-food crops, woody biomass and rice straw can be used for fermentative production, such production does not compete with food and feed production, and thus is desirable.

When non-edible biomass is used, not starch, but cellulose and hemicellulose constitute the main fermentation raw materials (carbon source). However, cellulose and hemicellulose cannot be directly used for lactic acid fermentation by a lactic acid bacterium, but require pretreatments (liquefaction and saccharification) for use in lactic acid fermentation.

Methods for the pretreatments can be roughly classified into physicochemical methods using acid, alkali, or the like, and biochemical methods using microorganisms or enzymes. However, as for the former type of methods, if it is intended to decompose cellulose into monosaccharides, treatments must be performed under relatively severe conditions, and fermentation inhibitors such as furfural are by-produced during such treatments. On the other hand, if the treatments are performed under relatively mild conditions, products of the treatments contains oligosaccharides derived from cellulose (cellooligosaccharides), and therefore there arises a disadvantage that, since cellooligosaccharides cannot be utilized by most of fermentative microorganisms, fermentation yield decreases. As for the latter biochemical methods, although research and development of enzymes themselves that decompose cellulose are advancing, enzymatic decomposition of cellulose into monosaccharides requires use of large amounts of various enzymes and long time. Furthermore, manufacturing cost of these cellulose decomposition enzymes is extremely high, and glucose (C6 saccharide) and cellobiose (C6 disaccharide) as the hydrolysis products are also potent inhibitors of CBH and BGL (Non-patent documents 1 to 3).

Further, if hemicellulose is hydrolyzed, xylose (C5 saccharide) and oligosaccharides thereof (C5 oligosaccharides) are obtained, and if they are used for lactic acid fermentation, molar yield of lactic acid is usually halved compared with the case of using C6 saccharides (Non-patent documents 4 to 7).

As for lactic acid production from non-edible biomass, there are a plurality of reports concerning heterolactic acid fermentation and D-lactic acid fermentation (Non-patent documents 4 to 10). However, there are extremely few examples of fermentative production of L-lactic acid as the raw material of poly-L-lactic acid from mixed saccharides derived from non-edible biomass as the raw material, and any practically usable bacterium has not been found so far.

PRIOR ART REFERENCES

Non-Patent Documents

Non-patent document 1: Romero-Garcia S, Hernandez-Bustos C, Merino E, Gosset G, Martinez A (2009) Homolactic fermentation from glucose and cellobiose using *Bacillus subtilis*. Microbial Cell Factories 8:23 doi:10.1186/1475-2859-8-23, http://www.microbialcellfactories.com/content/8/1/23

Non-patent document 2: Okano K, Zhang Q, Yoshida S, Tanaka T, Ogino C, Fukuda H, Kondo A (2010) D-lactic acid production from cellooligosaccharides and s-glucan using L-LDH gene-deficient and endoglucanase-secreting *Lactobacillus plantarum*. Appl Microbiol Biotechnol 85:643-650

Non-patent document 3: Joshi D S, M S Singhvi M S, Khire J M, Gokhale D V (2010) Strain improvement of *Lactobacillus lactis* for D-lactic acid production. Biotechnol Lett 32:1573-6776

Non-patent document 4 for lactic acid fermentation from xylose: K. Tanaka, A. Komiyama, K. Sonomoto, A. Ishizaki, S. J. Hall and P. F. Stanbury.: Two different pathways for D-xylose metabolism and the effect of xylose concentration on the yield coefficient of L-lactate in mixed-acid fermentation by the lactic acid bacterium *Lactococcus lactis* IO-1, Appl. Microbiol. Biotechnol., 60(1-2), 160-167 (October 2002)

Non-patent Document 5 for lactic acid fermentation from xylooligosaccharides: Hitomi Ohara, Michiko Owaki & Kenji Sonomoto.: Xylooligosaccharide fermentation with *Leuconostoc lactis*, J. Biosci. Bioeng., 101(5), 415-420 (May 25, 2006)

Non-patent document 6 for lactic acid fermentation from xylose: Hitomi Ohara, Michiko Owaki & Kenji Sonomoto.: Calculation of metabolites from xylose in *Lactococcus lactis*, J. Biosci. Bioeng., 103(1), 92-94 (Jan. 25, 2007)

Non-patent Document 7 for lactic acid fermentation from xylose: Mugihito Oshiro, Hideaki Shinto, Yukihiro Tashiro, Noriko Miwa, Tatsuya Sekiguchi, Masahiro Okamoto, Ayaaki Ishizaki & Kenji Sonomoto.: Kinetic modeling and sensitivity analysis of xylose metabolism in *Lactococcus lactis* IO-1, J. Biosci. Bioeng., 108(5), 376-384 (Nov. 25, 2009)

Non-patent document 8 for lactic acid production from cellulose by simultaneous saccharification and fermentation: S. Abe and M. Takagi.: Simultaneous saccharification and fermentation of cellulose to lactic acid, Biotechnol. Bioeng., 37, 93-96 (1991)

Non-patent document 9 for lactic acid production from cellulose by simultaneous saccharification and fermentation:

K. V. Venkatesh.: Simultaneous saccharification and fermentation of cellulose to lactic acid, Bioresour. Technol., 62, 91-98 (1997)

Non-patent document 10 for lactic acid bacteria that directly utilize xylan: M. Ishikawa, K. Nakajima, Y. Itamiya, S. Furukawa, Y. Yamamoto and K. Yamasato.: *Halolactibacillus halophilus* gen. nov., sp. nov. and *Halolactibacillus miurensis* sp. nov., halophilic and alkaliphilic marine lactic acid bacteria constituting a phylogenetic lineage in *Bacillus* rRNA group 1., Int. J. Syst. Evol. Microbiol., 55, 2427-2439 (2005)

SUMMARY OF INVENTION

Object to be Achieved by Invention

L-Lactic acid fermentation using non-edible biomass requires use of a mixture comprising oligosaccharides (C6 oligosaccharides, C5 oligosaccharides, etc.) or mixed saccharides (C6 saccharides, C5 saccharides, etc.) produced by enzymatic or physicochemical treatment of cellulose and hemicellulose as a raw material, so that simultaneous saccharification and fermentation are enabled.

Means for Achieving the Object

The inventors of the present invention screened microorganisms obtained from various natural sources, and thereby obtained a novel lactic acid bacterium capable of efficiently producing L-lactic acid of high optical purity from a saccharide mixture. Then, they variously examined the culture conditions therefor, and accomplished the present invention. The present invention thus provides the followings.

[1] A method for producing L-lactic acid, which comprises the step of culturing a lactic acid bacterium that can produce L-lactic acid in a medium containing any one selected from the group consisting of cellobiose, cellooligosaccharides, xylose, arabinose, and glucose derived from cellulose and/or hemicellulose as a substrate to obtain L-lactic acid.

[2] The method according to [1], wherein the lactic acid bacterium is a lactic acid bacterium belonging to *Enterococcus mundtii*.

[3] The method according to [1] or [2], wherein the medium contains cellooligosaccharides as substrates, and the cellooligosaccharides contain cellotriose and cellotetraose.

[4] The method according to any one of [1] to [3], wherein the medium contains xylose as a substrate, and further contains glucose and/or cellobiose as a substrate, and concentration of xylose is 10 to 150 g/L.

[5] The method according to any one of [1] to [4], which is carried out in an open system and/or a non-sterilized medium.

[6] The method according to [5], wherein fermentation is repeated batchwise.

[7] The method according to any one of [1] to [6], wherein the biomass raw material is a non-edible biomass raw material.

[8] A method for producing poly-L-lactic acid, which comprises the step for producing L-lactic acid defined in any one of [1] to [7], and the step of polymerizing L-lactic acid.

MODES FOR CARRYING OUT THE INVENTION

Figure 1:
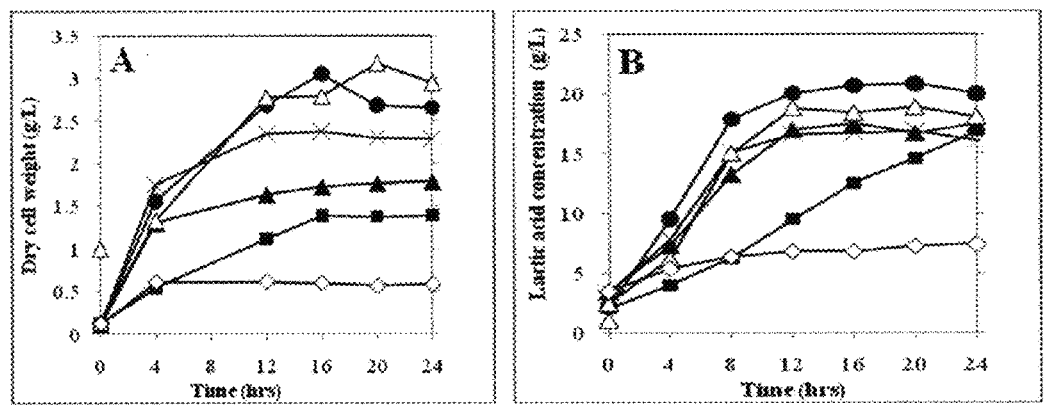
FIG. 1 Profiles of cell growth (A) and lactic acid production (B) from cellobiose by QU 25 during normal batch fermentation in modified MRS medium (under pH-controlled or pH uncontrolled condition). Symbols: ◇, pH-uncontrolled condition; ■, pH set at 5.5; ▲, pH set at 6.0; ×, pH set at 6.5; ●, pH set at 7.0; △, pH set at 7.5.

The present invention provides a method for efficiently producing high purity L-lactic acid using a lactic acid bacterium.

[Lactic Acid Bacterium]

The term "lactic acid bacterium" used in the present invention refers to a bacterium that produces a large amount of lactic acid (50% or more of acids produced when it ferments a carbohydrate), favorably grows in a medium containing a carbohydrate, is Gram positive, shows no motility, and does not sporulate, unless especially indicated. The lactic acid bacteria used in the present invention include microorganisms belonging to the genus *Enterococcus, Lactobacillus, Bifidobacterium, Lactococcus, Pediococcus,* or *Leuconostoc*.

A lactic acid bacterium suitable for use in the present invention can be obtained from a sample obtained from a natural source by screening performed as follows. A small amount of the sample is added to a modified MRS medium (for example, the MRS medium containing cellobiose or glucose at a concentration of 2% [wt/vol]), culture is performed at 30° C. for 3 days or 7 days under an anaerobic condition, a part of the culture is serially diluted, and spread on a CM-cellobiose agar plate, and collection of colonies, dilution, and streak culture are appropriately performed to obtain single colonies. Isolated bacteria are tested for catalase in a conventional manner, and catalase negative bacteria are further subjected to selection using the CM-cellobiose agar medium to select those providing high yield and optical purity of lactic acid.

For the present invention, a lactic acid bacterium belonging to *Enterococcus mundtii* can be preferably used. In particular, *Enterococcus mundtii* NITE BP-965 can be especially preferably used. This strain was isolated by the inventors of the present invention from a stool sample of sheep collected in the Fukuoka City Zoological Garden (1-1, Minami-koen, Chuo-ku, Fukuoka-shi, Fukuoka-ken, Japan), and deposited at the independent administrative institution, National Institute of Technology and Evaluation, NITE Patent Microorganisms Depositary (2-5-8, Kazusakamatari, Kisarazu-shi, Chiba-ken, 292-0818, Japan) on Jul. 15, 2010 with as accession number NITE BP-965. In this specification, this strain may be called QU25.

This QU25 strain has the following characteristics concerning lactic acid fermentation:

(1) the bacterium can produce L-lactic acid having an optical purity of 99.0% or higher (preferably 99.5% or higher, more preferably 99.75% or higher, further preferably 99.9% or higher); and (2) the bacterium can produce 20 g/L of L-lactic acid when it is cultured at 43° C. for 20 hours or more with controlling pH to be 7.0 in a medium containing 20 g/L of cellobiose.

When it is described that a bacterium "can produce" lactic acid in the present invention, it means that the bacterium can produce lactic acid at specified purity and concentration under conditions within the defined ranges for the items of which specific ranges are defined (for example, temperature and time) and conditions suitable for fermentative production of lactic acid for the items of which ranges are not specified (for example, stirring velocity, and presence or absence or degree of aeration), unless especially indicated. Further, the term substrate concentration means substrate concentration at the time of start of culture (also referred to as initial concentration), unless especially indicated.

The present invention provides not only QU25, but also a microorganism equivalent thereto, specifically, the following microorganisms:

[1] A lactic acid bacterium belonging to *Enterococcus mundtii*, which has the following characteristics:

(1) the bacterium can produce L-lactic acid having an optical purity of 99.0% or higher (preferably 99.5% or higher, more preferably 99.75% or higher, further preferably 99.9% or higher); and (2) the bacterium can produce 20 g/L of L-lactic acid when it is cultured at pH 7.0 and 43° C. for 20 hours or more in a medium containing 20 g/L of cellobiose;

[2] A lactic acid bacterium having the same bacteriological characteristics as those of QU25, as shown below:

1. Morphology: coccus
2. Biochemical characteristic: catalase negative
3. Motility: none
4. Relation to oxygen: facultatively anaerobic
5. Ability to produce L-lactic acid by homolactic acid fermentation using glucose as a substrate
6. The following saccharide utilization pattern:

TABLE 1

| Sugar | | Sugar | |
|---|---|---|---|
| Glycerol | + | Salicine | + |
| Erythriol | − | Cellobiose | + |
| D-Arabinose | − | Maltose | + |
| L-Arabinose | + | Lactose | + |
| D-Ribose | + | Melobiose | + |
| D-Xylose | + | Sucrose | + |
| L-Xylose | − | Trehalose | + |
| Adonitol | − | Inulin | − |
| α-Methyl-D-xyloside | − | Melezitose | − |
| Galactose | + | D-Raffinose | − |
| D-Glucose | + | Starch | ± |
| Fructose | + | Glycogen | − |
| D-Mannose | + | Xylitol | − |
| L-Sorbose | − | α-Gentibiose | + |
| Rhamnose | + | D-Turanose | − |
| Dulcitol | − | D-Lyxose | − |
| Inositol | − | D-Tagatose | + |
| Mannitol | + | D-Fucose | − |
| Sorbitol | + | L-Fucose | − |
| α-Methyl-D-mannoside | − | D-Arabitol | − |
| α-Methyl-D-glucoside | − | L-Arabitol | − |
| N-Acetyl-glucoamine | + | Gluconate | − |
| Amygdalin | + | 2-Keto-gluconate | − |

TABLE 1-continued

| Sugar | | Sugar | |
|---|---|---|---|
| Arbutine | + | 5-Keto-gluconate | − |
| Esculine | + | | |

+ positive,
− negative

Those skilled in the art can obtain a microorganism equivalent to QU25 by screening microorganisms isolated from appropriate natural sources with reference to Example 1 of this specification. The various values concerning lactic acid fermentation mentioned in the present invention (for example, pH, saccharide concentration, and optical purity) can be appropriately measured by conventional methods. When the values differ depending on measurement methods, the values are values measured by the methods described in the example section of this specification, unless especially indicated. Further, the various kinds of fermentation parameters concerning lactic acid fermentation mentioned in the present invention are well known to those skilled in the art, and refer to those described in the example section of this specification, unless especially indicated.

QU25 and equivalent microorganisms thereof can be favorably cultured by using the MRS medium containing 10 g of peptone, 8 g of beef extract, 4 g of yeast extract, 20 g of glucose, 1 g of Tween 80, 2 g of $K_2HPO_4$, 5 g of sodium acetate trihydrate, 2 g of diammonium hydrogencitrate, 0.2 g of $MgSO_4.H_2O$ and 0.05 g of $MnSO_4.nH_2O$ in 1 L of distilled water (or a modified medium thereof) supplemented with a substrate such as glucose or cellobiose at an appropriate concentration.

In this specification, the present invention may be explained by exemplifying a case of using QU25. Such explanation can also be applied to a case of using another suitable lactic acid bacterium such as a microorganism equivalent to QU25, unless especially indicated.

[Influence of pH]

When pH is controlled to be low within the range of 5.5 to 6.0, cell growth of QU25 may be inhibited compared with the case of controlling pH to be 6.5 to 7.5. It is considered that it cannot grow at a low pH because of the poor resistance thereof to free acids ($H^+$). At pH 5.5 to 6.0, it extremely slowly consumes saccharides, and saccharides may not be completely consumed. The maximum lactic acid production rate may become higher as pH becomes higher, and may be maximized around pH 7.5. By controlling pH, there can be obtained a maximum lactic acid production rate several times higher than that obtainable without controlling pH.

Therefore, in the present invention, from the viewpoint of production efficiency, pH of the environment is preferably 6.0 or higher, more preferably 6.5 or higher, further preferably 6.7 or higher. As for the upper limit of pH, it is preferably lower than 7.5, more preferably 7.4 or lower, further preferably 7.3 or lower, in any case. The optimum pH is, for example, 7.0. Such an environmental pH range is probably preferred also from the viewpoint of optical purity of produced lactic acid.

[Influence of Temperature]

QU25 can maintain favorable biological activities over a wide temperature range of 30 to 45° C. concerning lactic acid production and lactic acid yield. In particular, in the range of 40 to 44° C., it can exhibit the maximum growth rate and the maximum lactic acid production rate. At a high temperature exceeding 45° C., QU25 may exhibit neither favorable cell growth nor high lactic acid production.

Therefore, from the viewpoint of efficient production of L-lactic acid, the temperature is preferably 30° C. or higher, more preferably 35° C. or higher, further preferably 40° C. or higher, in the present invention. As for the upper limit of the temperature, it is probably preferably lower than 45° C., more preferably lower than 44° C., in any case. The optimum temperature is, for example, 43° C.

[Influence of Substrate (Carbon Source)]

In the present invention, as for a component contained in the environment for the lactic acid bacterium, the expression that a component is contained "as a substrate" means that the component is contained in such an amount (concentration) that the microorganism can utilize the component.

QU25 can consume cellobiose of various concentrations like glucose. Saccharide consumption rates thereof for glucose and cellobiose can be approximated.

Therefore, according to the present invention, L-lactic acid of high purity and high concentration can be produced at high yield by using a saccharide mixture of glucose and cellobiose.

Common saccharification processes using lignocellulose provide a raw material containing many kinds of saccharides. Therefore, in order to maximize product yield and productivity by using a saccharification raw material derived from lignocellulose, it is desirable to completely utilize the mixed saccharides. However, since most of microorganisms preferentially utilize glucose compared with the other saccharides, when mixed saccharides are used for lactic acid production, saccharides are consecutively utilized, and therefore productivity reduces in many cases. However, according to the present invention, not only cellobiose can be efficiently utilized, cellobiose and glucose can be simultaneously consumed, and therefore it can be expected that saccharides produced from a cellulosic material by saccharification can be completely utilized at high efficiency and high speed. The present invention is the first invention concerning simultaneous utilization of glucose and cellobiose for lactic acid production by a microorganism.

Glucose concentration and cellobiose concentration of the environment used in the present invention can be appropriately determined by those skilled in the art so that the total amount of the substrates becomes 0.5 to 50% (by weight) based on the medium. Typically, initial glucose concentration and cellobiose concentration or those throughout the culture period may be independently 5 g/L or higher, preferably 20 g/L or higher, more preferably 50 g/L higher, further preferably 100 g/L or higher. In any case, glucose concentration and cellobiose concentration may be independently 400 g/L or lower, 300 g/L or lower, or 250 g/L or lower.

The glucose concentration and cellobiose concentration of the environment can be determined so that the weight ratio of glucose:cellobiose becomes 1:0.01 to 100, more specifically 1:0.1 to 10.

In the present invention, when a value is mentioned for concentration or ratio of a component, the value is used on weight basis, unless especially indicated. Further, a value mentioned for concentration or ratio in an environment is an initial value (at the time of the start of culture) or a value throughout the culture period, unless especially indicated.

According to the study of the inventors of the present invention, under the conditions mentioned in the examples of this specification, the growth behavior of QU25 observed at a cellobiose concentration of 150 g/L in the environment was similar to that observed at a lower concentration. No change of the growth behavior at the high saccharide concentration suggested that there was substantially no substrate inhibition against growth of QU25. However, lactic acid yield reduced in connection with increase of cellobiose concentration. It is considered that this was induced due to product inhibition or depletion of nutrient required for the lactic acid production, or combination of these, since it was reported that the substrate concentration did not generally significantly affect the yield and production amount. From the economical point of view, it is desirable to use high saccharide concentration in the lactic acid production. The upper limit of the cellobiose concentration for the present invention can be determined also from such a point of view. In the present invention, the maximum concentration of cellobiose in the environment may be 100 g/L.

Figure 6:
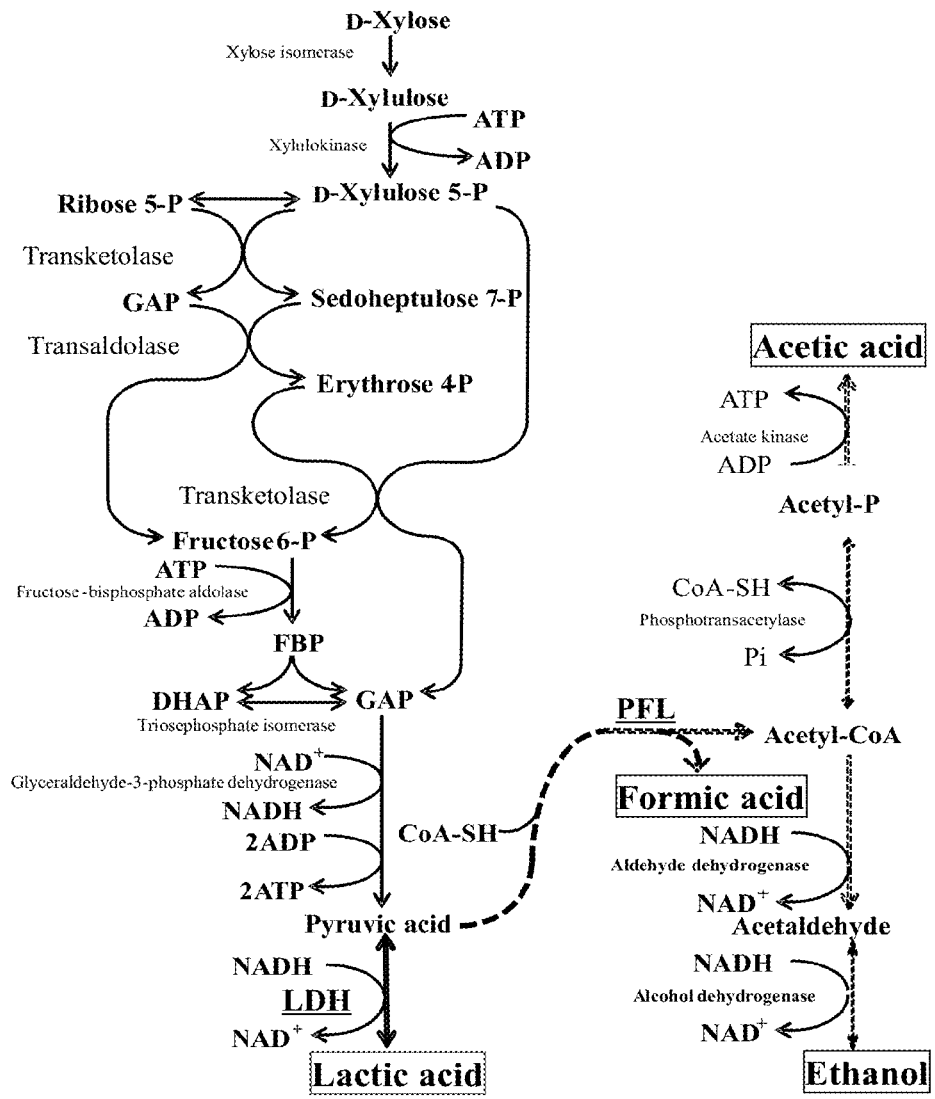
FIG. 6 Predicted pathway for xylose metabolism in QU 25. The key enzymes, LDH and PFL are underlined. Fermentation products; lactic acid, formic acid, acetic acid and ethanol are framed. Pathway for formic acid, acetic acid and ethanol from pyruvate is shown by dashed arrows. P, phosphate; FBP, fructose 1,6-diphosphate; GAP, glyceraldehyde 3-phosphate; DHAP, dihydroxyacetone phosphate.

According to the study of the inventors of the present invention, fermentation yield provided by QU25 may vary depending on xylose concentration. More precisely, when only xylose is used as a substrate, a relatively low xylose concentration may invite production of by-products, and low lactic acid yield, whereas a relatively high xylose concentration may provide substantially no production of by-products, and production of lactic acid at high yield. However, a further higher concentration of xylose may invite reduction of production rate or yield, and it is understood that it is due to inhibition by the high substrate concentration. For reference, expected xylose metabolic pathway of QU25 is shown in FIG. 6.

Therefore, from such a viewpoint as mentioned above, the xylose concentration used in the present invention is preferably 20 g/L or higher, more preferably 40 g/L or higher. In any case, it is preferably 150 g/L or lower, more preferably 103 g/L or lower (691 mM or lower).

According to the present invention, xylose is favorably consumed, and also by using xylose, lactic acid can be produced around pH 7.0 and 43° C. as in the case of using glucose or cellobiose.

According to the present invention, lactic acid can be produced by using a mixture of glucose and xylose as a substrate. When such a mixture is used, typically, initial glucose concentration and xylose concentration may be independently 5 to 250 g/L. Further, glucose concentration and xylose concentration in the environment may be independently determined, and may be determined so that less than one part by weight, more specifically, less than 0.75 part by weight, of xylose is used with respect to 1 part by weight of glucose. With such a weight ratio, the saccharides are consumed in the same manner at any concentrations.

In the present invention, lactic acid can be produced by using a mixture of glucose, xylose, and cellobiose as a substrate. In such a case, concentrations of the saccharides may be independently determined, and may be determined so that independently less than one part by weight, more specifically, less than 0.75 part by weight, of each of xylose and cellobiose is used with respect to 1 part by weight of glucose. In such an embodiment, glucose and cellobiose may be quickly consumed first. It is considered that such quick consumption of cellobiose, which is a potent cellulase inhibitor, is extremely advantageous for commercial production of lactic acid from lignocellulose type biomass.

As described above, in the present invention, when only xylose is used at a relatively low concentration as a substrate, small amounts of by-products may be produced, but when xylose is used as a mixture with glucose and cellobiose, production of by-products may decrease. In general, when xylose is used with other saccharides in the present invention, concentration of xylose may be 5 g/L or higher, preferably 10 g/L, more preferably 15 g/L. As for the upper limit, the concentration may be 150 g/L, preferably 103 g/L, in any case.

QU25 can utilize cellooligosaccharides, i.e., cellotrioses (C6 trisaccharides), cellotetraoses (C6 tetrasaccharides), and cellopentoses (C6 pentasaccharides). In particular, it can produce L-lactic acid (optical purity, 100%) from cellotrioses and cellotetraoses at a yield of about 100%.

Therefore, according to the present invention, the following effects can be expected:
(1) Pretreatment process of non-edible biomass can be simplified, and cost thereof can be reduced;
(2) L-lactic acid yield from non-edible biomass can be substantially improved; and
(3) When an enzymatic decomposition reaction is used for the pretreatment process, the necessity for taking inhibition of the enzymatic reaction by oligosaccharides into consideration is reduced.

Non-edible biomass is mainly constituted by cellulose, hemicellulose, and lignin. When it is physicochemically decomposed, they can be decomposed to monosaccharides, but severe conditions are required. The decomposition under such severe conditions requires high cost and labor, and may induce further decomposition of monosaccharides. On the other hand, if the treatment is performed under relatively mild conditions, a lot of oligosaccharides are produced in addition to monosaccharides. According to the present invention, xylooligosaccharides and cellooligosaccharides are effectively utilized.

Because of the characteristics of the present invention with respect to mixed saccharides, xylose, and cellooligosaccharides, it can be said that the present invention can be applied to simultaneous saccharification and fermentation from a biomass raw material. In particular, application to simultaneous saccharification and fermentation using non-edible biomass can be expected. As for the simultaneous saccharification and fermentation, Non-patent documents 8 and 9 mentioned above can be referred to.

From the viewpoint of efficiency (for both velocity and yield, no production of by-products), glucose is preferred as the substrate for producing L-lactic acid. However, when non-edible biomass is used as a raw material, there cannot be a carbon source consisting only of glucose, and a mixture containing pentoses such as xylose and arabinose and oligosaccharides thereof in addition to hexoses such as glucose, which are produced by a pretreatment of cellulose or hemicellulose, must be actually used as the carbon source. Therefore, there is desired a bacterial strain having various characteristics, for example, such characteristics that it can utilize such carbon sources as mentioned above, efficiently produce L-lactic acid (for both velocity and yield, and no production of by-products), and suffer from less substrate and product inhibition, and less catabolite suppression. According to a preferred embodiment of the present invention, QU25 can be used as such a strain.

[Open System Culture]

The lactic acid production according to the present invention can be performed in an open system or under a non-sterilized condition. The "open system" or "non-sterilized" condition includes no sterilization of a medium used for the production, and no need to perform takeover from one batch culture to next batch culture under a sterilized condition, when lactic acid is produced batchwise.

The lactic acid production according to the present invention can be carried out by repeated batch system.

The open or non-sterilized production system can (i) avoid the Maillard reaction during sterilization, (ii) reduce necessity of apparatus and energy consumption; and (iii) simplify the process and reduce labor, and therefore it is preferred (Bioresource Technology, 101 (2010) 6494-6498).

Further, the repeated batch operation can save both time and labor compared with the batch system. Such saving includes shorter time required for washing and sterilizing fermentation tank, omissibility of time to prepare seed, high growth ratio, and short main culture time provided by a large initial inoculation volume.

By combining the open system and the repeated batch operation, it is possible to establish an operation strategy for attaining further excellent energy efficiency and further saving labor and time.

Any open repeated batch system has not been reported for lactic acid bacteria. It is considered that an open repeated batch system realizes extremely easier operation and more excellent energy efficiency of L-lactic acid production. However, the strain used for such a system must be strong, and in particular, from the viewpoint of production of extremely optically pure lactic acid, it must be resistant to increase in possibility of contamination during repetition of batches in an open system.

To date, only one paper has been released concerning the open fermentation production of lactic acid with a bacterium (Bioresource Technology, 101 (2010) 6494-6498 mentioned above). The authors of this paper used strains of *Lactobacillus casei*, which is a lactic acid bacterium, and a *Bacillus* bacterium, which is a non-lactic acid bacterium. However, although their report mentioned various data and kinetic parameters for the strain of the *Bacillus* bacterium, it does not mentioned data for the strain of *Lactobacillus* bacterium except for the optical purity of 96 to 98.4%. As a view of the inventors of the present invention, the lactic acid concentration obtained by them was low, residual glucose concentration was high (about 30 to 50 g/L in almost all the cases), the fermentation time was long (up to 37 to 47 hours), and the productivity was lower than that obtained by the inventors of the present invention.

The present invention provides lactic acid production based on an open repeated batch system using a lactic acid bacterium for the first time, and according to an embodiment of the present invention utilizing an open repeated batch system, L-lactic acid of high optical purity can be produced at a high production rate as high as 14.1 g/L/h.

[Biomass Raw Material]

The "biomass (raw material)" referred to in the present invention means renewable organic resources derived from organisms except for fossil resources, unless especially indicated. For the present invention, any biomass raw materials that can be used as a raw material for lactic acid fermentation can be used, regardless of location of generation, present utilization state, and form thereof. Examples of the biomass raw material include sugar cane, rice, corn, sweet potato, rapeseed, peanut, soybean, bagasse, leaves and stems, rice straw, chaff, wheat straw, mowed lawn generated in large quantities on golf courses etc., woodland remainder material, thinner timber, oil palm tree, scrap wood generated in sawmills (for example, end materials, sawdust, bark), construction and demolition waste (wood dust), used paper, livestock feces and urine, slaughter house residue, fish processing residue, biomass organic sludge generated as waste, pulp mill waste liquor, food processing residue, used edible oil, kitchen garbage, raw sludge, fishery product, kelp, and phytoplankton.

The "edible biomass (also referred to as sustenance biomass or food biomass) (raw material)" referred to in the present invention means a biomass raw material that can also be used as sustenance of human or livestock, unless especially indicated. The edible biomass includes sugar cane, rice, corn, and sweet potato.

The "non-edible biomass (raw material)" referred to in the present invention means a biomass raw material other than edible biomass raw material, unless especially indicated. In the present invention, it is preferable to use a non-edible biomass raw material.

[Use]

L-Lactic acid produced by the present invention can be used as a raw material of poly-L-lactic acid. Further, it can also be used as a raw material for producing a stereo complex of poly-L-lactic acid and poly-D-lactic acid. Such a stereo complex can be a biodegradable plastic showing high heat resistance.

Optically pure L-(+)-lactic acid can be polymerized to become a highly crystalline polymer suitable for manufacture of fibers and oriented films, and is also expected to be useful for the manufacture of liquid crystals.

Furthermore, poly-L-lactic acid is presently used for many medical uses. For example, it is used for suture, stent, dialysis medium, and drug delivery device. It is being evaluated also as a material for system engineering. Since it is biodegradable, it can also be used for the manufacture of bioplastic materials, and it is useful for the manufacture of loose-fill packaging materials, compost bags, food packaging materials, and disposable tableware. Therefore, poly-L-lactic acid has possibility as a resource recycling material suitable for use in sustainable social systems in future.

Although the present invention relates to production of L-lactic acid, products obtained according to the present invention may be referred to simply as "lactic acid" for convenience in this specification (for example, in the term "lactic acid production rate" etc.). Those skilled in the art can appropriately understand that the term "lactic acid" is used to refer to L-lactic acid from the context.

EXAMPLES

Analytical Methods

The following methods or equivalent analytical methods were used throughout the examples, unless especially indicated.

Cell density was analyzed by measuring the optical density of the cell suspension at a wavelength of 562 nm (OD562) with a spectrophotometer (UV-1600 visible spectrophotometer, Bio-spec, Shimadzu Co., Tokyo, Japan). Dry cell weight was calculated from the predetermined standard curve relating OD562 to dry weight.

pH was measured with a bench-top pH-meter (HM-25R).

Cellobiose and fermentation products were determined by using HPLC (US HPLC-1210, Jasco, Tokyo, Japan) equipped with a SUGAR SH-1011 column (Shodex, Tokyo, Japan). 1 ml aliquot of the sample cultures was centrifuged by using bench-top centrifuge (Tomy, micro centrifuge, Model MX-300) at 2000 g for 10 min at 4° C. after which the supernatant was diluted with ultra pure water, filtered through Dismic 13-HP045 filters (Advantec, Toyo, Japan) and then injected in the chromatograph under the conditions: column temperature of 50° C., 3 mM $HClO_4$ as mobile phase at a flow rate of 1.0 ml min-1 and an injection volume of 20 µl. The concentrations of residual sugars and fermentation products were calculated using calibration curves obtained from standard solutions.

The optical purity of lactic acid was measured using a BF-5 biosensor (Oji Scientific Instruments, Hyogo, Japan) according to the manufacturer's protocol.

[Fermentative Parameters]

The following fermentation parameters were used throughout the examples, unless especially indicated.

(1) Specific Growth Rate (μ)

The specific growth rate (μ) were calculated as follows:

$$\mu(h^{-1}) = \ln(x_2/x_1)/(t_2-t_1) \quad \text{[Formula 1]}$$

in which (x) is $OD_{562}$ value and (t) is the sampling time (h).

(2) Yield of Lactic Acid Based on Substrate Consumed (Y, g/g)

The yield of lactic acid based on substrate consumed (Y, g/g) was defined as the ratio of lactic acid produced (g/L) to sugar consumed (g/L).

(3) Lactic Acid Productivity

The lactic acid productivity was calculated as the ratio of lactic acid concentration (g/L) to the fermentation time (h) (calculation between each sampling period).

(4) Purity of L-Lactic Acid

The purity of L-lactate was evaluated as follows:

$$\% \text{ optical purity} = (L\text{-lactic add concentration} - D\text{-lactic acid concentration})/(L\text{-lactic add concentration} + D\text{-lactic add concentration}) \times 100 \quad \text{[Formula 2]}$$

(5) Values of Overall Sugar Uptake (qs) and Specific Lactic Acid Production Rate (qp)

The values of overall sugar uptake (qs) and specific lactic acid production rate (qp) of fermentation were calculated using the following formula:

$$qs = (1/x_{av})(\Delta s/\Delta t) \text{ and } qp = (1/x_{av})(\Delta p/\Delta t) \quad \text{[Formula 3]}$$

in which Δs and Δp are the changes in the sugar and lactic acid concentrations, respectively, over time period Δt; and $x_{av}$ is the average of cell mass concentration over Δt.

[Media]

Unless especially indicated, modified MRS (mMRS) medium was used, which contained the followings (per liter): 10 g peptone (Difco, Detroit, Mich.), 8 g beef extract (Nacalai Tesque, Kyoto, Japan), 4 g yeast extract (Nacalai Tesque), 2 g $K_2HPO_4$ (Nacalai Tesque), 5 g $CH_3COONa_3 \cdot H_2O$ (Nacalai Tesque), 2 g tri-ammonium citrate (Nacalai Tesque), 0.2 g $MgSO_4 \cdot 7H_2O$ (Nacalai Tesque), 0.05 g $MnSO_4 \cdot 4H_2O$ (Nacalai Tesque), 1 ml Tween 80 (Nacalai Tesque). Unless especially indicated, the medium supplemented with glucose at 10 g/L (1%) for refresh and pre-cultures, and at 20 g/L for main fermentation. Optionally, the medium supplemented with D-cellobiose (Sigma), glucose and/or arabinose at a predetermined concentration.

Example 1

Study of Culture Conditions (1) Materials and Methods

QU25 was used for this study.

A. Flask Culture

The culture stored in glycerol (1 ml) was inoculated to 9 ml of the mMRS medium enriched with saccharide (1% [wt/vol]) contained in 15-ml screw cap tubes (10% [vol/vol]), and incubated at 30° C. for 24 hours. A part of the obtained culture was inoculated into 100 ml of the mMRS-cellobiose (2% [wt/vol]) medium in a 200-ml volume flask (10% [vol/vol]), and cultured at 30° C. for 72 hours. pH at the start of the culture was 6.5.

B. Jar Fermenter Culture

Culture (4 ml) obtained by refreshment performed in the same manner as that used for the flask culture was transferred to fresh growth medium in 50-ml screw cap test tubes containing 36 ml of the same medium. The inoculum was incubated at 30° C. for 8 hours, and then inoculated into a jar fermenter at 10% [vol/vol].

Fermentation was carried out at an agitation rate of 200 rpm in a 1 L-volume jar fermenter (Biott, Tokyo, Japan) in a working volume of 0.4 L (0.2 L for culture at a sugar concentration of 150 g/L) using mMRS supplemented with various amounts of saccharides. The saccharide solution was autoclaved independently and mixed with the rest of mMRS medium.

At each sampling time, 5 ml of the cultures were removed aseptically from each jar, and frozen at −20° C. for further analysis. The samples were assayed for dry cell weight (DCW), residual saccharides and fermentation products.

In order to investigate optimum pH, assays were performed without and with control of pH during fermentation by addition of 5 M NaOH with a peristaltic pump connected to an automatic pH controller (PH C2201, Biott). pH was controlled at 5.5, 6.0, 6.5, 7.0, and 7.5, respectively. Growth was allowed at 30° C. for 24 hours, and then fermentation profile of the strain was measured.

In order to investigate the effect of temperature on lactic acid production, assays were performed at different temperatures controlled at 30, 37, 43, 45, 47 and 50° C., respectively, in pH-controlled fermentations at pH 7.0 with automatic addition of 5 M NaOH. Fermentations were carried out in mMRS-cellobiose (2.0% [wt/vol]).

The effect of saccharide mixture was studied by adding glucose and cellobiose at a ratio of 1:1 to the fermentation medium at concentrations of 10, 15, and 20 g/L for each. The effect of substrate concentration was studied in the mMRS medium having a cellobiose concentration of 50, 100 or 150 g/L, or a glucose concentration of 150 g/L. Fermentations were carried out at 43° C. and pH 7.0 (controlled by automatic addition of 10 M or 15 M NaOH) in all the cases. For the culture using saccharide concentrations of 150 g/L, 1%, 0.25% and 0.25% (wt/vol) of yeast extract was supplemented after 8, 60 and 96 hours, respectively.

(2) Results

A. Growth and Lactic Acid Production Profile Determined on the Basis of Time-Course Study Time-course study was conducted by flask culture to prepare growth and lactic acid production profiles of QU25 under the condition of not controlling pH. In this batch fermentation, the strain consumed cellobiose at an extremely low velocity (per volume). On the basis of DCW measurement, it was found that QU25 quickly grew, and the growth leveled at about 0.91 g/l of DCW (FIG. 1). After 21 hours, pH dropped to 4.85, and the maximum L-(+)-lactic acid production concentration was 7.04 g/l after 60 hours of incubation with no production of by-products.

B. Lactic Acid Fermentation Under pH-Controlled Condition

The results are shown in the following table.

TABLE 2

Effects of pH of culture medium on lactic acid fermentation from cellobiose by *Enterococcus mundtii* QU25[a].

| pH | $\mu_{max}$[b] ($h^{-1}$) | Maximum cell mass (g/l) | Maximum L-lactic acid produced (g/l) at indicated time | L-lactic acid yield[c] (%) | Maximum L-lactic acid productivity (g/l/h) |
|---|---|---|---|---|---|
| No control | 0.415 | 0.71 | 3.90 ± 0.09 (24 h) | 65.7 | 0.47 |
| 5.5 | 0.368 | 1.38 | 13.9 ± 0.76 (24 h) | 87.0 | 0.82 |
| 6.0 | 0.610 | 1.89 | 14.8 ± 0.89 (24 h) | 84.0 | 1.48 |

TABLE 2-continued

Effects of pH of culture medium on lactic acid fermentation from cellobiose by Enterococcus mundtii QU25[a].

| pH | $\mu_{max}$[b] (h$^{-1}$) | Maximum cell mass (g/l) | Maximum L-lactic acid produced(g/l) at indicated time | L-lactic acid yield[c] (%) | Maximum L-lactic acid productivity (g/l/h) |
|---|---|---|---|---|---|
| 6.5 | 0.672 | 2.37 | 14.7 ± 0.00 (20 h) | 86.6 | 1.81 |
| 7.0 | 0.635 | 3.04 | 18.7 ± 2.04 (20 h) | 94.4 | 2.10 |
| 7.5 | 0.575 | 3.17 | 16.4 ± 0.25 (20 h) | 83.0 | 2.20 |

[a]Fermentations were carried out at 30° C. and the indicated pH with initial cellobiose concentration 20 g/L. Averages with standard deviations are based on three independent fermentations.
[b]Maximum specific growth rate;
[c]Produced lactic acid (g/L) per consumed sugar (g/L)

Figure 2:
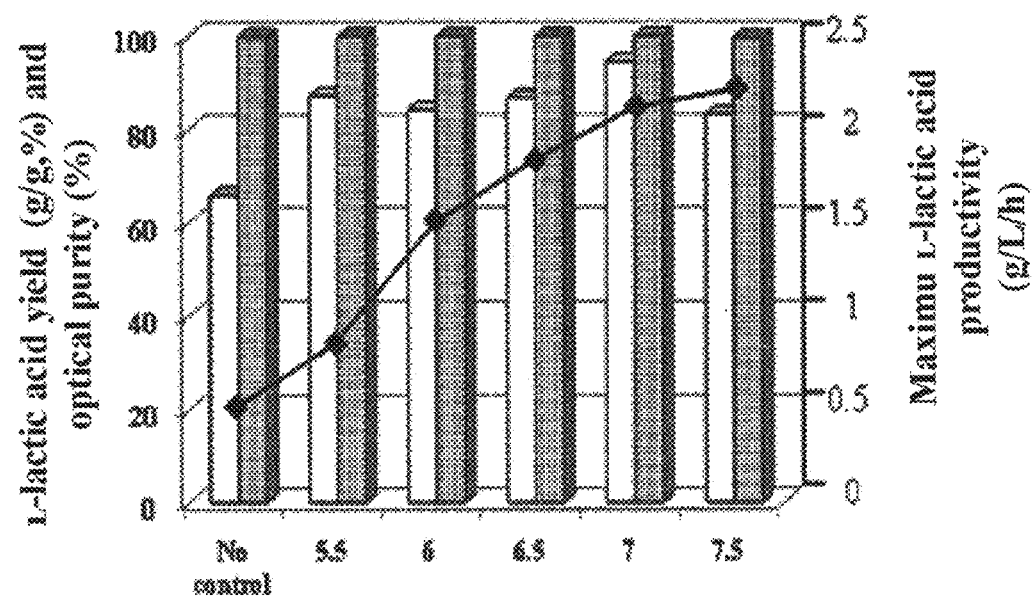
FIG. 2 Yield, optical purity and maximum lactic acid production rate of L-(+)-lactic acid productivity from cellobiose by QU 25 cultured in media set at different pH values. white bars, yield %; gray bars, optical purity %; closed diamond, maximum lactic acid productivity.

HPLC analysis results showed that the fermentation was homolactic acid fermentation, because no other component peaks appeared except for a very small amount of acetate as by-product. Yield, optical purity, and maximum production rate are shown in FIG. 2.

Low pH of 5.5 to 6.0 obviously inhibited cell growth, compared with higher pH values from 6.5 to 7.5. At pH values of from 5.5 to 6.0, cellobiose was consumed very slowly, and was not depleted until the end of fermentation. The maximum lactic acid production rate increased with increase of pH value to a value as high as 2.1 g/L/h at pH 7.0, which was approximately 4-fold higher than that obtained in non-pH-controlled fermentation. On the basis of the results shown in Table 2 also with consideration for lactic acid yield etc., it is considered that the optimal pH value is 7. At that pH, only 16 to 20 hours were required for the complete depletion of cellobiose.

C. Lactic Acid Fermentation at Various Temperatures

The results are shown in the following table.

TABLE 3

Effects of culture temperature on lactic acid fermentation from cellobioses by batch culture of Enterococcus mundtii QU25[a].

| Temperature (° C.) | $\mu_{max}$[b] (h$^{-1}$) | Maximum cell mass (g/L) | Maximum L-lactic produced (g/L) at indicated time | L-lactic acid yield[c] (%) | Maximum lactate productivity (g/L/h) |
|---|---|---|---|---|---|
| 30 | 0.640 | 3.17 | 20.3 ± 0.57 (20 h) | 104 | 2.54 |
| 37 | 0.662 | 2.88 | 20.2 ± 0.76 (20 h) | 102 | 3.07 |
| 43 | 0.675 | 2.64 | 20.4 ± 0.63 (20 h) | 104 | 3.44 |
| 45 | 0.400 | 1.72 | 17.9 ± 0.17 (16 h) | 93.0 | 1.77 |
| 47 | 0.200 | 0.52 | 5.80 ± 0.02 (16 h) | 103 | 0.46 |
| 50 | 0.136 | 0.36 | 3.05 ± 0.09 (24 h) | 60.0 | 0.30 |

[a]Fermentations were carried out with pH-controlled at 7.0 with initial cellobiose concentration 20 g/L. Averages with standard deviations are based on three independent fermentations.
[b]Maximum specific growth rate;
[c]Produced lactic acid (g/L) per consumed sugar (g/L)

QU25 showed favorable biological activities over a wide temperature range of 30 to 45° C. for lactic acid production and lactic acid yield. At 43° C., cellobiose was totally consumed by culture of 20 hours. However, although the lactic acid concentration was almost the same at 30 to 43° C., the maximal lactic acid productivity was increased from 2.54 g/L/h at 30° C. to 3.44 g/L/h at 43° C. with increase of the temperature. Similarly, the maximum growth rate increased with increasing temperature with the highest value of 0.675 h$^{-1}$ at 43° C. The cell growth entered the death phase right after the cellobiose substrate was depleted at high temperature while showed long stationary phase at lower temperature. At high temperatures above 45° C., QU25 did not show either good cell growth or high lactic acid production. Thus, the optimum temperature is considered to be 43° C.

D. Lactic Acid Fermentation from Glucose/Cellobiose Mixture

The results are shown in the following table.

TABLE 4

Lactic acid fermentation with mixture of glucose and cellobiose by Enterococcus mundtii QU25[a]

| Carbon source (g/L) | | $\mu_{max}$[b] (h$^{-1}$) | $X_{max}$ (g/L) | Maximum L-lactic acid (g/L) at indicated time | Yield of L-lactic acid to cell mass[c] ($g_{LA}/g_{DCW}$) | L-lactic acid yield[d] (%) | Average volumetric productivity[e] (g/L/h) |
|---|---|---|---|---|---|---|---|
| Glucose | Cellobiose | | | | | | |
| 10 | 10 | 0.668 | 3.04 | 18.9 ± 0.26 (6 h) | 6.20 | 97.0 ± 0.036 | 3.15 |
| 15 | 15 | 0.850 | 3.40 | 26.9 ± 0.02 (10 h) | 8.14 | 96.0 ± .0007 | 2.58 |
| 20 | 20 | 0.620 | 3.62 | 35.02 ± 0.1 (15 h) | 10.1 | 93.0 + 0.004 | 2.99 |

Figure 3:
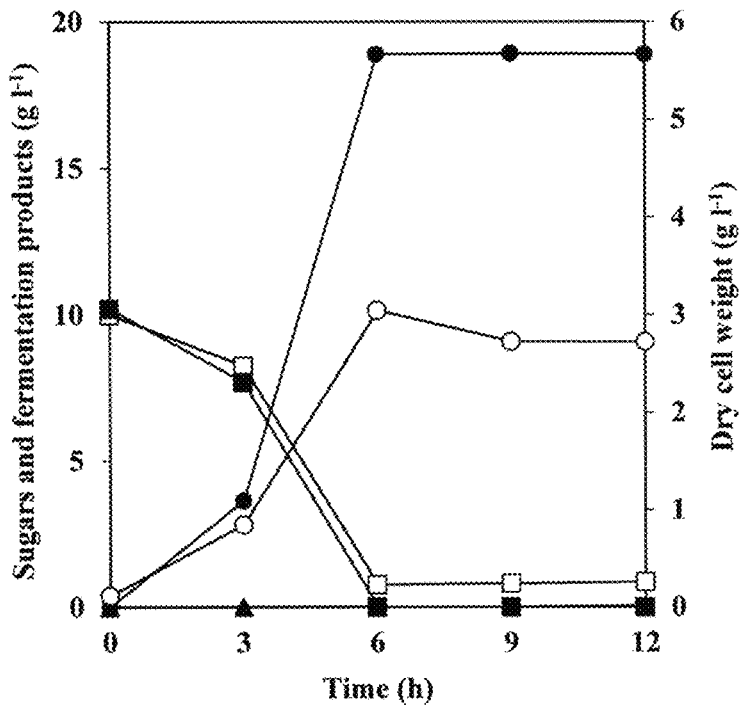
FIG. 3 Time courses of L-lactic acid production by QU 25 using a glucose/cellobiose mixture. The fermentation was carried out at 200 rpm, pH 7.0 and 43° C. in a 1-L jar fermentor with 0.4-L medium under normal batch fermentation. Symbols: ○, dry cell weight ●, lactic acid; □, cellobiose; ■, glucose. Data points represent the means and standard deviations of results from three independent experiments. The standard deviation is less than the size of symbol if no error bars are seen.

[a]Fermentations were carried out at 43° C. and pH 7.0. Averages with standard deviations are based on three independent fermentations.
[b]Maximum specific growth rate;
[c]Maximum produced lactic acid (g/L) per cell mass (g/L) at the indicated time;
[d]Produced lactic acid (g/L) per consumed sugar (g/L);
[e]During the exponential growth Saccharide consumption and lactic acid production at glucose and cellobiose concentrations of 10 g/L each are shown in FIG. 3. QU25 consumed cellobiose like glucose, and fermentation was completed within 6 hours. Sugar consumption rates for glucose and cellobiose were 1.69 g/L/h and 1.53 g/L/h, respectively, which were similar to each other.

With the saccharide mixture, lactic acid was produced at high concentration and high yield. These data suggested that QU25 simultaneously utilized the saccharides in the mixture like a single carbon source.

E. Influence of Cellobiose Concentration

The results are shown in the following table.

TABLE 5

Effect of sugar concentrations on lactic acid fermentation by Enterococcus mundtii QU25[a]

| Initial sugar concentration (g/L) | $\mu_{max}$[b] ($h^{-1}$) | Maximum cell mass (g/L) | Maximum L-lactic acid produced (g/L) at indicated time | L-lactic acid yield[c] (%) | Maximum L-lactic acid productivity (g/L/h) | Optical purity of L-lactic acid (%) |
|---|---|---|---|---|---|---|
| Cellobiose | | | | | | |
| 50.8 | 0.785 | 2.89 | 50.1 ± 0.82 (20 h) | 102 | 3.53 | 99.9 |
| 101 | 0.777 | 2.88 | 89.8 ± 1.00 (72 h) | 91.3 | 3.69 | 99.9 |
| 150.9 | 0.740 | 5.47 | 119 ± 3.70 (106 h) | 83.0 | 4.50 | 99.9 |
| Glucose | | | | | | |
| 150 | 0.582 | 4.18 | 124 ± 0.82 (120 h) | 83.6 | 5.36 | 99.9 |

[a]Fermentations were carried out at 43° C. and pH 7.0. Averages with standard deviations are based on three independent fermentations.
[b]Maximum specific growth rate;
[c]Produced lactic acid (g/L) per consumed sugar (g/L)

Figure 4:
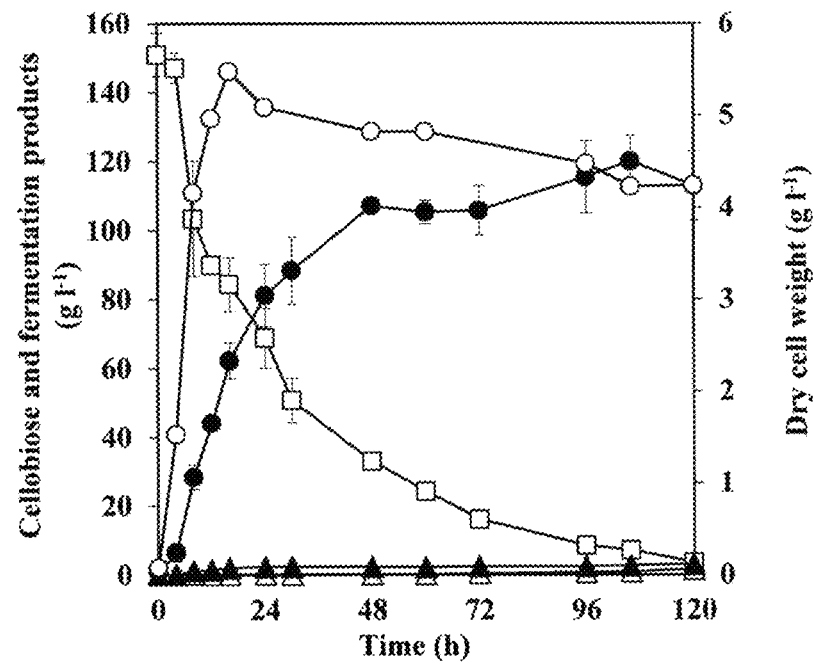
FIG. 4 Profiles of lactic acid production, cellobiose utilization, acetic acid production, ethanol production and growth, during lactic acid fermentation by QU 25 from 150 g $l^{-1}$ cellobiose. The fermentations were carried out at 200 rpm, 43° C., pH was maintained at 7.0 in a 1-L jar fermentor with 0.2-L medium. Symbols: Symbols: ○, dry cell weight ●, lactic acid; ■, acetic acid; ▲, ethanol; □, cellobiose. Data points represent the means and standard deviations of results from three independent experiments. The standard deviation is less than the size of symbol if no error bars are seen.

The fermentation profile observed at a cellobiose concentration of 150 g/L is shown in FIG. 4. The profile was generally similar for different substrate concentrations, except for the fermentation time, which was extended in connection with increase of the substrate concentration. Interestingly, there was a very short induction phase, and thereafter, the cell growth rates were more or less the same in the exponential phases. Cell growth behavior suggested no substrate inhibition on the growth of QU25. The cell growth curves passed a short stationary phase, and then entered into the death phase. With 50 g/l of cellobiose, fermentation was almost completed within 20 hours, while about 50 hours were further required for consuming 100 g/l of cellobiose, and about 76 hours were further required for consuming 150 g/l of cellobiose. Further, the fermentation profile for 150 g/L of glucose was substantially the same as that for 150 g/L of cellobiose.

On the basis of the results mentioned above, it can be concluded that the substrate inhibition action in lactic acid fermentation can be disregarded.

Example 2

Influence of Xylose (1) Method

As the medium, there was used the mMRS medium used in the above-mentioned examples, which was supplemented with xylose as a saccharide. Xylose concentration was 10 g/L at the time of the refreshment. Further, for examination of influence of pH control and temperature, a jar fermenter (1 L volume) was used, and the final xylose concentration was 166 mM (25 g/L). With three levels of the final xylose concentration, 334 mM (50.1 g/L), 480 mM (72.0 g/L), and 691 mM (103 g/L), the fermentation profile was examined. The culture conditions of QU25 were the same as those of Example 1.

(2) Results

A. Influence of pH Control and Temperature

The results are shown in the following table.

TABLE 6

L-Lactic acid fermentation with xylose by Enterococcus mundtii QU25 under different pH and temperature.[a]

| pH controlled | Temperature (° C.) | $X_{max}$ (g/L) | Maximum lactic acid production at the indicated time (mM) ± SD | | Lactic acid yield (mol/mol)[b] | Lactic acid productivity[c] (mM/L/h) |
|---|---|---|---|---|---|---|
| | | | (mM) ± SD | (h) | | |
| — | 30 | 1.00 | 35.0 ± 0.07 | 24 | 1.05 | 1.45 |
| 6.0 | 30 | 1.60 | 66.0 ± 7.60 | 24 | 1.30 | 2.75 |
| 6.5 | 30 | 2.95 | 126 ± 15.0 | 24 | 0.89 | 5.25 |
| 7.0 | 30 | 3.27 | 131 ± 1.57 | 24 | 0.82 | 5.45 |
| 7.5 | 30 | 3.60 | 87.0 ± 1.17 | 24 | 0.54 | 3.62 |
| 7.0 | 37 | 3.27 | 141 ± 20.0 | 24 | 0.82 | 5.87 |
| 7.0 | 41 | 3.30 | 155 ± 2.90 | 24 | 0.82 | 6.45 |
| 7.0 | 43 | 3.22 | 200 ± 3.10 | 16 | 1.13 | 12.5 |

TABLE 6-continued

L-Lactic acid fermentation with xylose by *Enterococcus mundtii* QU25 under different pH and temperature.[a]

| pH controlled | Temperature (°C.) | $X_{max}$ (g/L) | Maximum lactic acid production at the indicated time (mM) ± SD | (h) | Lactic acid yield (mol/mol)[b] | Lactic acid productivity[c] (mM/L/h) |
|---|---|---|---|---|---|---|
| 7.0 | 45 | 2.87 | 168 ± 0.70 | 16 | 1.04 | 10.5 |
| 7.0 | 47 | 0.33 | 15.0 ± 0.11 | 24 | 0.88 | 0.63 |

[a]Xylose concentration at the beginning of fermentation is 166 mM. Averages with standard deviations are based on three independent fermentations.
[b]Lactic acid produced (mole)/consumed xylose (mole)
[c]Maximum lactic acid produced/the indicated time At 30° C., the highest lactic acid production rate was observed at pH 7.0. At pH 7.0, in the range of 30 to 43° C., the lactic acid production rate increased as temperature rose. It was found that QU25 favorably consumed xylose, and the culture conditions around pH 7.0 and 43° C. were preferred also in view of xylose consumption.

B. Influence of Xylose Concentration

Figure 5:
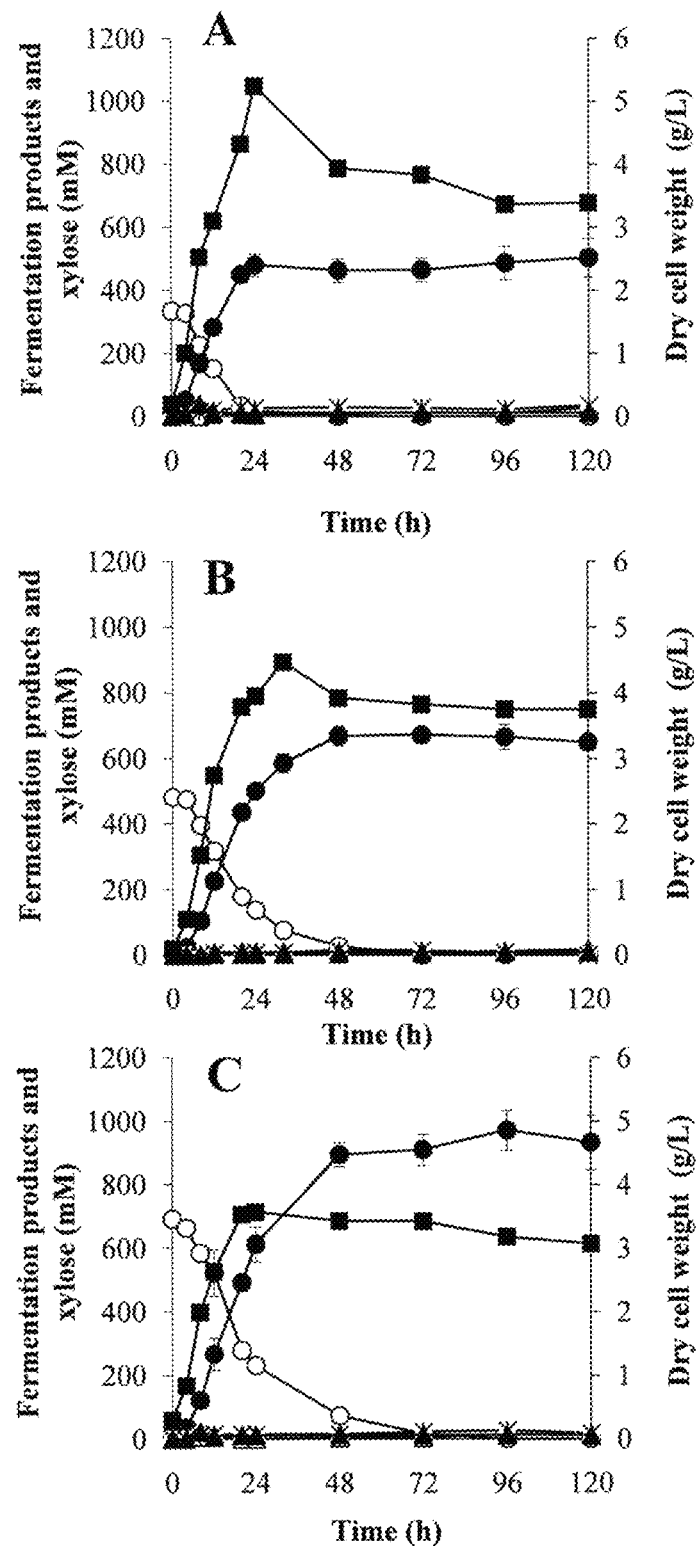
FIG. 5 Profiles of lactic acid fermentation with xylose by QU 25. The fermentations were conducted in 1-L jar fermentor with 0.4-L working volume at 43° C., pH 7.0, and 200 rpm. The initial xylose concentrations were 334 mM (A), 480 mM (B) and 691 mM (C). Symbols: ○, xylose concentration; ●, lactic acid concentration; △, acetic acid concentration; ▲, formic acid concentration; □, ethanol concentration; ■, dry cell weight. Data points represent the means and standard deviations of results from three independent experiments. The standard deviation is less than the size of symbol if no error bars are seen.

The results are shown in the following table and FIG. 5.

TABLE 7

Lactic acid fermentation with high concentration of xylose by *Enterococcus mundtii* QU25[a]

| Initial xylose concentration (mM) | Maximum cell mass (g/L) | Maximum lactic acid produced (mM) | Yield of products (mol-product/mol-consumed xylose) | | | | Maximum specific productivity[c] (mmol/g [DCW] of cells per h) | Lactate/acetate (mol/mol) |
|---|---|---|---|---|---|---|---|---|
| | | | Lactic acid[b] | Acetic acid | Formic acid | Ethanol | | |
| 334 | 5.24 | 490 | 1.51 ± 0.18 | 0.08 ± 0.01 | 0.03 ± 0.01 | 0.1 ± 0.03 | 16.4 | 18.3 |
| 480 | 4.47 | 668 | 1.47 ± 0.06 | 0.01 ± 0.004 | 0.04 ± 0.03 | 0.03 ± 0.02 | 17.7 | 134 |
| 691 | 3.56 | 964 | 1.41 ± 0.09 | 0.00 | 0.02 ± 0.01 | 0.009 ± 0.001 | 16.4 | unlimited |

[a]Fermentations were done at 43° C. and pH 7. Averages with standard deviations are based on three independent fermentations.
[b]The maximum theoretical yield for lactic acid by pentose phosphate/glycolytic pathway (1.67 mol of lactic acid per mol of xylose).
[c]Maximum specific productivity for lactic acid
[d]Maximum lactic acid produced/production time With three levels of the xylose concentration, 334 mM (50.1 g/L, FIG. 5A), 480 mM (72.0 g/L, FIG. 5B), and 691 mM (103 g/L, FIG. 5C), the fermentation profile was examined. Only small amounts of acetic acid (≤17 mM), formic acid (≤13 mM) and ethanol (≤34 mM) were produced. Such a phenomenon is very rare in lactic acid fermentation from C5 saccharide using a wild strain, and suggests that lactic acid can be highly efficiently obtained from a C5 saccharide.

With the xylose concentration of 691 mM, the production rate and the yield decreased (data are not shown). It was understood that this was because of inhibition by the high substrate concentration. Although fermentation performed with high sugar concentration is desirable from the economical aspect, it was considered that practical xylose concentration for the lactic acid production by QU25 was 691 mM.

Example 3

Examination of Influence of Xylose Concentration on Fermentation Profile

Since it was elucidated by the study at an early stage that xylose concentration influenced on the fermentation charac- teristics, i.e., rates of products such as lactic acid, the details thereof were investigated.

(1) Method

Batch culture of QU25 was performed at pH 7.0 and 43° C., which are the optimal fermentation conditions, with changing xylose concentration.

(2) Results

The results are shown in the following table.

TABLE 8

Effect of xylose concentration on lactate production by QU 25

| Initial concentration of xylose (g/l) | Products (g/l) | | | | Yield coefficient of lactate (mol/mol-xylose consumed) |
|---|---|---|---|---|---|
| | Lactate | Acetate | Formate | Ethanol | |
| 6.18 | 0.89 | 1.50 | 2.60 | 1.32 | 0.25 |
| 11.6 | 2.99 | 1.97 | 3.75 | 2.28 | 0.44 |
| 15.1 | 5.51 | 2.40 | 4.48 | 2.90 | 0.63 |
| 18.5 | 8.26 | 2.43 | 4.54 | 3.42 | 0.78 |
| 27.5 | 18.0 | 1.15 | 2.99 | 3.08 | 1.17 |
| 39.6 | 29.5 | 1.41 | 3.45 | 3.01 | 1.26 |
| 51.4 | 46.9 | 1.70 | 0.00 | 1.89 | 1.51 |
| 71.5 | 61.1 | 0.29 | 0.00 | 1.08 | 1.47 |
| 103 | 89.6 | 0.00 | 0.00 | 1.47 | 1.41 |
| 150 | 86.6 | 0.22 | 0.00 | 0.15 | 1.16 |

Culture condition: pH 7.0, 43° C.

It was elucidated that the fermentation yield provided by QU25 changed depending on the substrate concentration. That is, at a low xylose concentration, by-products were generated, and the yield of lactic acid became low, but at a high xylose concentration, by-products such as acetic acid or formic acid were scarcely produced, and the yield of lactic acid became high.

On the basis of these results, it became clear that L-lactic acid could be produced at high concentration and high yield from a high concentration xylose preparation by using QU25 substantially without production of by-products.

Example 4

Cellooligosaccharide Utilization Test (1) Method

As the medium, there was used the mMRS medium used in the above-mentioned examples, which was supplemented with cellooligosaccharides (4.23 g/L of cellotriose, 2.67 g/L of cellotetraose, or 3.64 g/L of cellopentose) as a saccharide. Culture was started by inoculating 10% of QU25 cultured in the mMRS-cellobiose medium. The culture was performed at 43° C. and initial pH 7.0 (not controlled).

(2) Results

The results are shown in the following table.

TABLE 9

Utilization of cellooligosaccharides by *Enterococcus mundtii* QU 25

|  | $\mu_{max}$ (h−1) | $X_{max}$ (g/L) | Initial sugar (g/L) | Residual sugar (g/L) | Lactic acid produced (g/L) | Time of sampling (h) | Lactic acid yield (g/g) | Optical purity of lactic acid (%) |
|---|---|---|---|---|---|---|---|---|
| Cellotriose | 0.44 | 0.96 | 4.23 | 0.90 | 3.30 | 14 | 0.99 | 100 |
| Cellotetraose | 0.38 | 0.56 | 2.67 | 0.75 | 2.03 | 6 | 1.05 | 100 |
| Cellopentose | 0.16 | 0.26 | 3.64 | 3.12 | 0.55 | 14 | 0.80 | 99 |
| Medium components | 0.16 | 0.23 | 0.94 | 0.65 | 0.43 | 14 |  | 99 |

"Medium components" indicate a system using the medium not containing saccharide source,
$\mu_{max}$ represents the maximum specific growth rate, and
$X_{max}$ represents the maximum cell amount.

As shown in the above table, as a result of performing a utilization test using cellotriose (C6 trisaccharide), cellotetraose (C6 tetrasaccharide), and cellopentose (C6 pentasaccharide), L-lactic acid (optical purity, 100%) was produced at a yield of about 100% from cellotriose and cellotetraose. It was demonstrated that QU25 efficiently metabolized the cellooligosaccharides to produce L-lactic acid.

Example 4

Arabinose Utilization Test

Fermentation characteristics of the QU25 strain for arabinose, which is a pentose (C5 monosaccharide) like xylose, were examined.

4-1. Influence of pH on Lactic Acid Production from Arabinose (1) Method

As the medium, the mMRS medium supplemented with arabinose (200 mM) was used. QU25 cultured in the mMRS-arabinose medium and in the growth phase was inoculated (10%), and cultured at 43° C. and pH 7.0 at the time of the start of the culture without controlling pH thereafter, or with controlling pH to 6.0, 6.5, 7.0, or 7.5 (by automatic addition of 10 M or 15 M NaOH).

(2) Results
The results are shown in the following table.

TABLE 10

Bach fermentation with arabinose by *Enterococcus mundtii* QU 25

| pH | Xmax (g/l) | μmax (h−1) | Arabinose consumed (mM) | Lactate (mM) | Acetate (mM) | Formate (mM) | Ethanol (mM) | Yield coefficient of products (mol/mol) | | | | Pmax (mM/h) | Time (h) |
|---|---|---|---|---|---|---|---|---|---|---|---|---|---|
| | | | | | | | | Lactate | Acetate | Formate | Ethanol | | |
| No control | 1.13 | 0.354 | 46.13 | 72.49 ± 1.34 | 6.6 ± 2.6 | 0 | 0 | 1.57 ± 0.029 | 0.143 | 0 | 0.000 | 11.21 | 24 |
| 6 | 2.02 | 0.394 | 134.25 | 193.6 ± 0.24 | 2.06 ± 0.56 | 0 | 0 | 1.44 ± 0.002 | 0.015 | 0 | 0.000 | 9.94 | 28 |
| 6.5 | 3.93 | 0.455 | 195.5 | 224.39 ± 2.43 | 30.175 ± 0.47 | 56.65 ± 1.20 | 0 | 1.147 ± 0.007 | 0.154 | 0.290 | 0.000 | 19.21 | 24 |
| 7 | 4.15 | 0.559 | 201.88 | 190.29 ± 0.36 | 28.44 ± 0.346 | 76.37 ± 0.70 | 69.6 ± 6.94 | 0.94 ± 0.0003 | 0.141 | 0.378 | 0.345 | 17.94 | 24 |
| 7.5 | 3.6 | 0.536 | 199.1 | 149.73 ± 1.01 | 64.42 ± 4.75 | 136.7 ± 4.52 | 70.8 ± 7.48 | 0.75 ± 0.003 | 0.324 | 0.687 | 0.687 | 17.22 | 24 |

When the culture was performed at 43° C. without controlling pH, about 46 mM of arabinose was utilized, and about 72 mM of lactic acid was produced. The lactic acid yield was 1.57 mol/mol. This high lactic acid yield is close to the maximum theoretical yield obtainable through the PP/glycolytic pathway (1.67 mol/mol). Further, because of the generation of very small amounts of by-products such as formic acid and acetic acid, it is considered that purification of lactic acid can be performed at low cost.

When the culture was performed with controlling pH to be 6.0, by-products were generated in the smallest amounts, and about 193 mM of lactic acid was produced. The lactic acid yield in this case was 1.44 mol/mol. The maximum cell amount was smaller than that obtained at pH 6.5 to 7.5. Further, when the culture was performed with controlling pH to be 6.5, the highest lactic acid production amount of 224 mM was obtained, but by-products were also generated at high concentrations. Furthermore, when the culture was performed at pH 7.0 or higher, generation of by-products increased, and lactic acid yield markedly decreased. On the basis of these results, it is considered that pH is preferably controlled to be 6.0 or 6.5.

4-2. Examination of Arabinose Concentration (1) Method

As in 4-1, 10% of QU25 cultured in the mMRS-arabinose medium and in the growth phase was inoculated, and cultured at 43° C. with controlling pH to be 6.5 or 6.0. Arabinose concentration of the medium was 107.6, 199.55, 202.14, 326, 477.02, or 606.93 mM.

(2) Results

The results obtained with controlling pH to be 6.5 are shown in the following table.

TABLE 11

Effect of arabinose concentration on lactate production by QU 25 (pH-controlled at 6.5)

| Arabinose Conc. (mM) | Xmax (g/l) | μmax (h−1) | Arabinose consumed (mM) | Lactate (mM) | Acetate (mM) | Formate (mM) | Ethanol (mM) | Yield coefficient of products (mol/mol) | | | | Pmax (mM/h) | Time (h) |
|---|---|---|---|---|---|---|---|---|---|---|---|---|---|
| | | | | | | | | Lactate | Acetate | Formate | Ethanol | | |
| 107.6 | 2.16 | 0.414 | 101.42 | 111.03 | 19.67 ± 0.27 | 0 | 0 | 1.09 | 0.196 | 0 | 0 | 5.75 | 36 |
| 199.55 | 3.24 | 0.587 | 192.26 | 248.6 ± 4.38 | 17.42 ± 1.41 | 27.82 ± 0.37 | 0 | 1.29 | 0.09 | 0.14 | 0 | 16.18 | 36 |
| 202.14 | 3.93 | 0.455 | 195.5 | 224.39 ± 2.43 | 30.175 ± 0.47 | 56.65 ± 1.20 | 0 | 1.147 ± 0.007 | 0.154 | 0.290 | 0.000 | 19.21 | 24 |
| 326 | 3.76 | 0.689 | 318.3 | 452.3 | 9.58 ± 0.12 | 38.91 ± 0.307 | 0 | 1.41 | 0.03 | 0.12 | 0 | 30.4 | 31 |
| 477.02 | 3.59 | 0.378 | 455.7 | 593.2 | 0 | 0 | 0 | 1.32 | 0 | 0 | 0 | 26.77 | 72 |
| 606.93 | 3.61 | 0.344 | 590.73 | 763.1 | 0 | 0 | 0 | 1.29 | 0 | 0 | 0 | 29.48 | 96 |

When the culture was performed at pH 6.5, 763 mM of lactic acid was produced from arabinose at an initial concentration of 606.9 mM. By-products were not produced, and the lactic acid yield based on arabinose was 1.29 mol/mol. However, with an arabinose concentration of 326 mM or lower, by-products were produced. Since formic acid was mainly by-produced, it was suggested that the major metabolic pathway of arabinose was the PP/glycolytic pathway.

On the basis of these results, it is expected that the metabolisms and controls thereof for xylose and arabinose, which are both pentoses, are different in the QU25 strain.

The results obtained by performing the culture at pH 6.0 are shown in the following table.

QU25 consumed the saccharides in a similar manner at all the concentrations. By-products were not generated, and the optical purity was also high.

B. Glucose/Xylose/Cellobiose Mixture

In the same manner as that used in A of this example, except that cellobiose was further added, the lactic acid fermentation from the mixture was examined.

Figure 8:
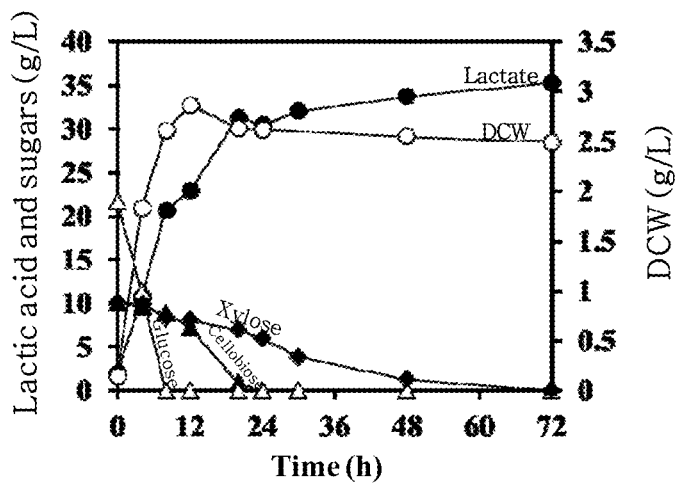
FIG. 8 Lactic acid production by QU 25 using a glucose/xylose/cellobiose mixture. DCW, Dry Cell Weight. The fermentation was carried out at 200 rpm, pH 7.0 and 43° C.

The results are shown in FIG. 8. Glucose and cellobiose were quickly consumed. It is considered that the quick consumption of cellobiose, which is also a potent cellulase inhibitor, would be very advantageous in the commercial lactic acid production from biomass containing a lot of cellulose and hemicellulose.

TABLE 12

Effect of arabinose concentration on lactate production by QU 25 (pH-controlled at 6.0)

| Arabinose Conc. (mM) | Xmax (g/l) | μmax (h−1) | Arabinose consumed (mM) | Lactate (mM) | Acetate (mM) | Formate (mM) | Ethanol (mM) | Yield coefficient of products (mol/mol) | | | | Pmax (mM/h) | Time (h) |
|---|---|---|---|---|---|---|---|---|---|---|---|---|---|
| | | | | | | | | Lactate | Acetate | Formate | Ethanol | | |
| 208.82 | 2.02 | 0.394 | 134.25 | 193.6 ± 0.24 | 2.06 ± 0.56 | 0 | 0 | 1.44 ± 0.002 | 0.015 | 0 | 0.000 | 9.94 | 28 |
| 211.82 | 2.09 | 0.374 | 204.96 | 278.3 | 0.07 | 0 | 0 | 1.36 | 0.07 | 0 | 0 | 12.15 | 72 |
| 329.4 | 4.04 | 0.668 | 318 | 445.14 | 0 | 0 | 0 | 1.39 | 0.000 | 0.000 | 0.000 | 37.81 | 32 |
| 478.53 | 0.98 | 0.121 | 95.86 | 109.55 | 0 | 0 | 0 | 1.14 | 0.000 | 0.000 | 0.000 | 8.66 | 72 |
| 604.53 | 0.498 | 0.081 | 100.5 | 120.66 | 0 | 0 | 0 | 1.2 | 0.000 | 0.000 | 0.000 | 5.6 | 108 |

From arabinose at an initial concentration of 329.4 mM, 445.14 mM of lactic acid was produced. By-products were not produced, and the yield was 1.39 mol/mol. However, with a higher arabinose concentration (>329 mM), both the arabinose consumption and lactic acid production were markedly decreased by the substrate inhibition. It is clearly different from the fermentation behavior observed at pH 6.5 shown in Table 11, and they were interesting fermentation phenomena in which the metabolism significantly changed by the small difference of the controlled pH values, 6.0 and 6.5.

Example 5

Lactic Acid Production from Saccharide Mixture

A. Glucose/Xylose Mixture

Lactic acid fermentation from a mixture of glucose and xylose at a weight ratio of 2:1 was examined. Fermentation was carried out at 43° C. with controlling pH to be 7.0 (by automatic addition of 10 M or 15 M NaOH) in all the cases.

Figure 7:
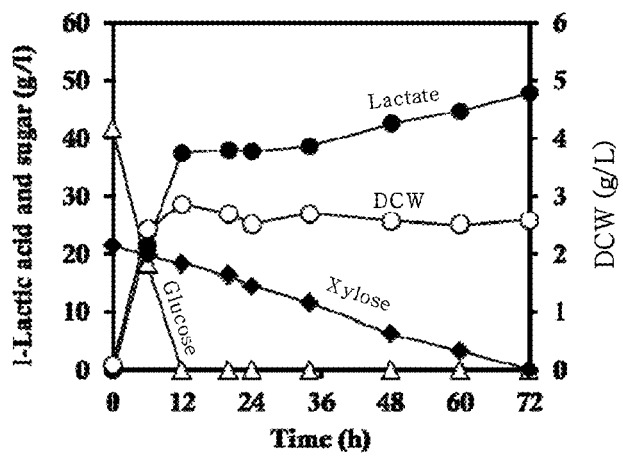
FIG. 7 Lactic acid production by QU 25 using a glucose/xylose mixture. DCW, Dry Cell Weight. The fermentation was carried out at 200 rpm, pH 7.0 and 43° C.

The results are shown in the following table. The results of the culture performed with an initial glucose concentration of 40 g/L are shown in FIG. 7.

Figure 9:
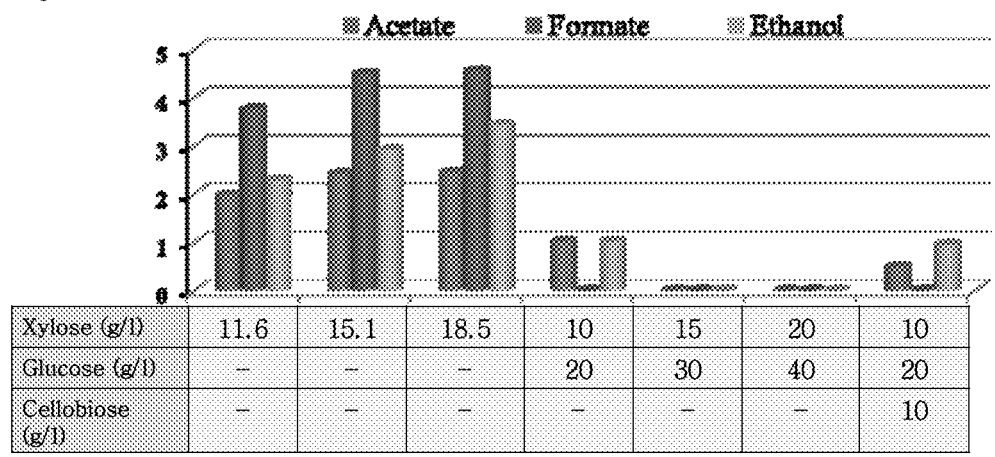
FIG. 9 Gist of by-products from lactic acid productions by QU 25 using a glucose/xylose mixture or a glucose/xylose/cellobiose mixture FIG. 10 Time courses of open repeated batch fermentation with *Enterococcus mundtii* QU 25 for L-lactic acid production. (A) Batches number 1-11 with glucose, (B) Batch number 12 with mixed glucose and xylose. Symbols: ▲, glucose (g/l); △, xylose (g/l); ○, lactic acid (g/l). The numbers on the arrows indicate the batch number. The standard errors were calculated from duplicate measurements.
Figure 10:
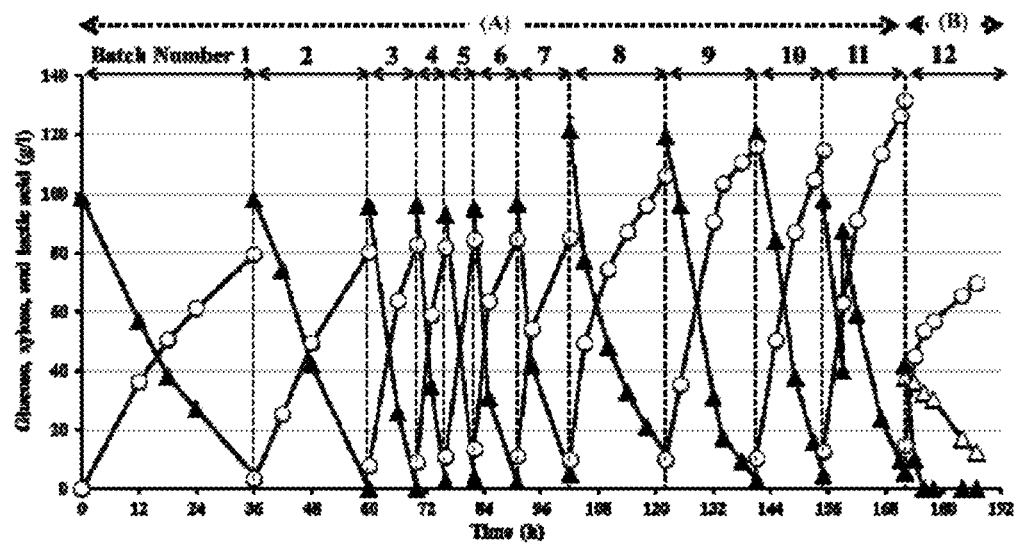

Further, when only xylose is used at a low concentration (<25 g/L) as the carbon source, small amounts of by-products were generated, but when it was used as a mixture with other saccharides, generation of by-products markedly decreased (FIG. 9).

Example 6

Non-Sterilized Repeated Fermentation Using QU25

According to the study of the inventors of the present invention, it was found that QU25 was a more heat-resistant strain compared with other lactic acid bacteria, and it could be used in non-sterilized fermentation.

In this example, repeated batch fermentation was performed by using QU25 under a non-sterilized condition.

(1) Methods

Refreshed and pre-cultured (MRS-20 g/l glucose) QU 25 cells were cultured at 43° C.

pH was controlled at 7.0. As a neutralizing agent, 10 N NaOH for 1-7 batches and 15 N NaOH for batches 8-12.

No sterilization of media was carried out at all 12 batches. Cells were collected by centrifugation at the end of each batch

TABLE 13

Lactate Production from Glucose/Xylose Mixture

| Carbon source (g/l) | | $\mu_{max}{}^a$ (h−1) | $X_{max}{}^b$ (g/l) | Lactic acid (g/l) at indicated time (h) | Lactate yield (g/g) | Maximum $P_{LA}$ (g/l/h) | $C_{acetate}$, $C_{ethanol}$, $C_{formate}$ (g/l) |
|---|---|---|---|---|---|---|---|
| Glucose | Xylose | | | | | | |
| 20 | 10 | 0.481 | 2.38 | 25.3 (48 h) | 0.842 | 3.57 | 1.01, 1.01, 0.0 |
| 30 | 15 | 0.571 | 3.11 | 37.6 (48 h) | 0.830 | 3.60 | 0.00 |
| 40 | 20 | 0.550 | 2.86 | 47.9 (72 h) | 0.750 | 3.50 | 0.00 |

[a]Maximum specific growth rate;
[b]Maximum cell mass (run/cycle) and used at 10% for the next batch (run) except batch number-6 the inoculum was 14%.

Open repeated fermentation was conducted for Twelve cycles. Cycles 1-10, and cycle were 12 batches; cycle number 11 only was fed batch). The cultivation time for each batch was varied up to culture condition.

In the first five runs, mMRS media with 100 g/l glucose was used to investigate the influence of batch repetition on L-lactic acid production. In batch 6, higher cell density was used at (14%) to test whether the same nutrient that used in the first five batches could support the growth of higher initial cell density In batches 7-10, nutrient requirement was studied by using yeast extract at 5, 10 and varied glucose concentration as mentioned in each run. In batch 11, fed batch was conducted to use higher substrate concentration. In batch 12 mixed sugar fermentation was conducted

TABLE 14

In brief and more clarification

Batch 1-6: mMRS media with ca 100 g/l glucose
Batch 7: mineral of mMRS with 5 g/l yeast extract (no peptone, no beef extract) andca 100 g/l glucose
Batch 8: mineral of mMRS with 5 g/l yeast extract (no peptone, no beef extract) and ca130 g/l glucose
Batch 9: mineral of mMRS with 10 g/l yeast extract (no peptone, no beef extract) andca 130 g/l glucose
Batch 10: mMRS with 130 g/l glucose
Fed-Batch 11: mMRS fed batch, initial glucose was ca 100 g/l then fed with 50 g/l after 4 h from the beginning of fermentation
Batch 12: Mixed sugar fermentation with 45 g/l glucose and 37.5 g/l xylose (mol:mol)

(2) Results
The Results are shown in the following table.

Figure 12:
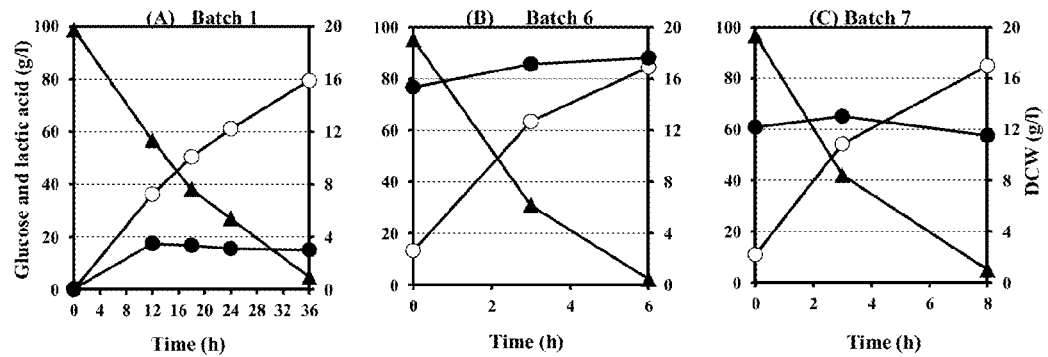
FIG. 12 Kinetics of the (A) first batch, (B) sixth batch, and (C) seventh batch of open repeated batch fermentation with *E. mundtii* QU 25 grown in MRS (A and B), and mMRS (C; supplemented with 5 g/l-yeast extract instead of 10 g/l-peptone/8 g/l-beef extract/4 g/l-yeast extract). Initial glucose concentration was 100 g/l. Symbols: ▲, glucose (g/l); ○, lactic acid (g/l); ●, DCW (g/l).

In batche 7, we studied the effect of nutritional conditions on lactate production and productivity by using only 5 g/l (instead of 4 g/l yeast+10 g/l peptone+8 g/l beef extract of mMRS media). Interestingly, slightly higher level of lactate was produced at the same yield as previous batch however the initial cell density was lower than previous batches, i.e batches 4-6 (FIG. 12).

More interestingly by adding higher substrate concentration (batch 8) with same medium of previous batch (minerals with only 5 g/l yeast extract), lactate yield and production level were improved. In contrast, lactate productivity was significantly decreased to half (i e from 10.61 g/l/h to 5.29 g/l/h). (the above table and FIG. 13).

In batch 9 we used 10 g/l of yeast extract (instead of 5 g/l) at the same initial glucose concentration (130 g/l). We found that lactate concentration, yield, and productivity were slightly improved (the above table).

Figure 11:
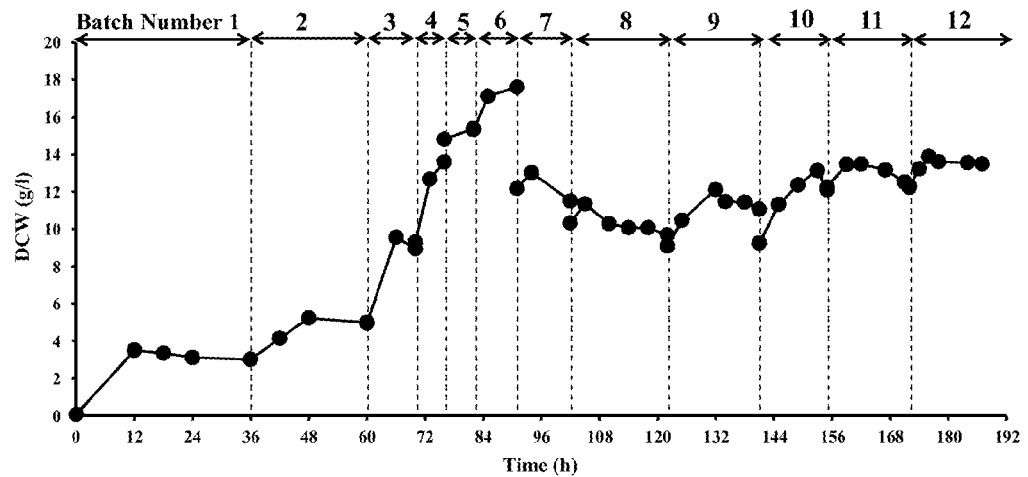
FIG. 11 Profiles of cell growth (DCW, g/l) of open repeated batch fermentation with *Enterococcus mundtii* QU 25 for l-lactic acid production. (A) Batches number 1-11 with glucose, (B) Batch number 12 with mixed glucose and xylose. The numbers on the arrows indicate the batch number. The standard errors were calculated from duplicate measurements.

In the case of use low yeast extract only (5 g/l) as nitrogen source, we noticed that cell density gradually decreased during fermentation, while with MRS the cell density is increased. (FIG. 11)

Figure 13:
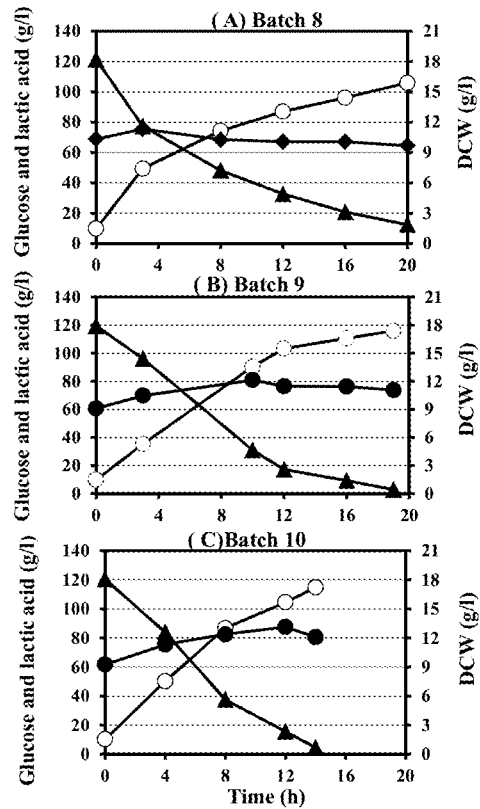
FIG. 13 Kinetics of the (A) eighth batch, (B) ninth batch, and (C) tenth batch of open repeated batch fermentation with *E. mundtii* QU 25 grown in minerals of MRS (A and B), instead of peptone/beef extract/yeast extract, supplemented with only 5 g/l yeast extract (A) and 10 g/l yeast extract (B), and complete MRS (C). Initial glucose concentration was 130 g/l. Symbols: ▲, glucose (g/l); ○, lactic acid (g/l); ●; DCW (g/l).

In batch 10, we used MRS with 130 g/l glucose, All fermentation parameters were increased (table 1). We could obtain 114.7 g/l lactic acid at yield of 0.90 g/g and high productivity of 8.1 g/l/h (FIG. 13)

Figure 14:
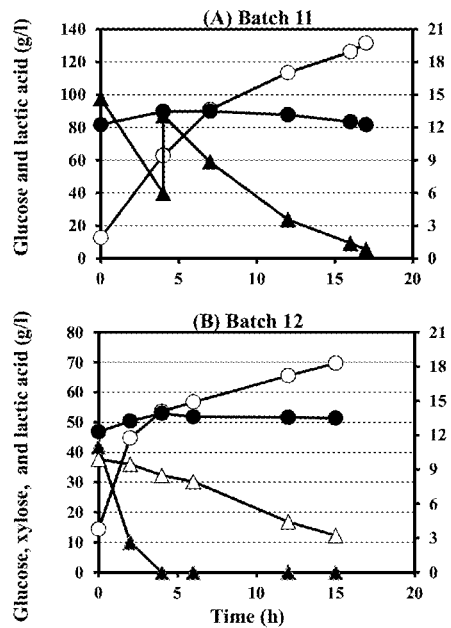
FIG. 14 Kinetics of the (a) $11^{th}$ fed-batch, and (b) $12^{th}$ mixed sugars batch of open repeated fermentation with *E. mundtii* QU 25 grown in minerals of MRS. (A) Initial glucose concentration was 100 g/l and fed with 50 g/L after 4 h from the beginning of fermentation. (B) initial glucose and xylose were 45 and 37.5 g/L, respectively. Symbols: ▲, glucose (g/l); Δ, xylose ○, lactic acid (g/l); ●; DCW (g/l).

We changed the mode of fermentation to fed batch at cycle (run) number 11, we could obtain 131.6 g/l lactic acid from 144.5 g/l glucose at high yield and productivity of 7.74 g/l/h and 0.85 g/g, respectively. (FIG. 14)

Finally we used mixed sugars (glucose and xylose) at mole:mole ratio. Interestingly, lactate was produced homofermentatively at high yield of 0.82 g/g and high productivity of 4.64 g/l/h.

TABLE 15

Kinetic parameters of open fermentative production of lactic acid with E. mundtii QU 25

| Batch number | Initial sugar (g/L) | Maximum DCW (g/l) | L-lactic acid (g/l) | Time (h) | L-Lactic acid Yield (g/g) | Productivity P (g/l/h)* | Maximum productivity $P_{max}$ (g/l/h) | Optical purity (%) | Residual sugar (g/l) |
|---|---|---|---|---|---|---|---|---|---|
| Glucose | | | | | | | | | Glucose |
| 1 | 100 | 3.49 ± 0.006 | 79.4 ± 0.27 | 36 | 0.84 | 2.21 | 3.01 | 99.4 | 4.69 |
| 2 | 100 | 5.23 ± 0.006 | 80.2 ± 0.49 | 24 | 0.78 | 3.34 | 3.99 | 99.0 | 0.00 |
| 3 | 100 | 9.56 ± 0.012 | 82.6 ± 0.17 | 10 | 0.78 | 8.26 | 9.33 | 99.3 | 0.00 |
| 4 | 100 | 13.6 ± 0.037 | 81.6 ± 0.47 | 6 | 0.77 | 13.6 | 16.6 | 99.5 | 2.32 |
| 5 | 100 | 15.4 ± 0.037 | 84.1 ± 0.81 | 6 | 0.83 | 14.0 | 12.3 | 99.9 | 3.60 |
| 6 | 100 | 17.6 ± 0.012 | 84.5 ± 1.04 | 6 | 0.76 | 14.1 | 16.7 | 99.6 | 2.16 |
| 7 | 100 | 13.0 ± 0.012 | 84.9 ± 0.91 | 8 | 0.81 | 10.61 | 14.5 | 99.4 | 4.98 |
| 8 | 130 | 11.3 + 0.012 | 105.9 ± 0.18 | 20 | 0.88 | 5.29 | 13.2 | 99.3 | 12.5 |
| 9 | 130 | 12.1 ± 0.025 | 115.8 ± 0.13 | 19 | 0.91 | 6.09 | 8.49 | 99.5 | 2.79 |
| 10 | 130 | 13.1 ± 0.00 | 114.7 ± 0.14 | 14 | 0.90 | 8.19 | 9.95 | 99.5 | 4.54 |
| 11 | 150 | 13.5 ± 0.24 | 131.6 ± 1.34 | 17 | 0.85 | 7.74 | 12.6 | 99.5 | 5.50 |
| Glucose/xylose | | | | | | | | | Glu/Xylose |
| 12 | 45/37.5 | 13.9 ± 0.024 | 69.7 ± .40 | 15 | 0.82 | 4.64 | 15.2 | 99.1 | 0.0/12.3 |

*These data is depending on real glucose concentration that was added to the medium (i.e. 100 or 130 or 150 g/l), and depending on at real lactic acid concentration at o time (0 g/l)
*Note that, the lactate concentration appeared at zero time is due to high speed consumption of glucose and its conversion to lactic acid in the first few minutes during the preparation of each batch until sampling time (Just Few minutes)

In the first 6 batches, lactate productivity increased gradually with an increase of cell density (FIG. 1). Lactate productivity is significantly increased from 2.21 g/l/h at first batch to 14.1 g/l/h at batch 6. Lactate production rate is almost stable with almost same lactate yield ~80% (see to the above table).

Optical purity of lactic acid was kept high at all runs (≥99%) (the above table).

These data is the first report demonstrating the capability of repeated open batch with LAB for optically pure lactate production. Open repeated batch with QU 25 was successfully performed for 12 cycles without any loss in fermentation capacity.

The invention claimed is:

1. A method for producing L-lactic acid, which comprises the step of culturing one or more *Enterococcus mundtii* strains that can produce L-lactic acid in a medium comprising one or more saccharide selected from the group consisting of cellobiose and cellooligosaccharide as a substrate to obtain L-lactic acid, wherein the one or more *Enterococcus mundtii* strains have a negative saccharide utilization pattern for L-Xylose.

2. The method according to claim 1, wherein the one or more *Enterococcus mundtii* strains is *Enterococcus mundtii* NITE BP-965.

3. The method according to claim 1, wherein the medium comprises cellooligosaccharide as substrates, and the cellooligosaccharides are cellotriose and cellotetraose.

4. The method according to claim 1, wherein fermentation is repeated batchwise.

5. A method for producing poly-L-lactic acid, which comprises the steps of:

culturing one or more *Enterococcus mundtii* strains that can produce L-lactic acid in a medium comprising one or more saccharide selected from the group consisting of cellobiose and cellooligosaccharide, as a substrate to obtain L-lactic acid; and polymerizing L-lactic acid to obtain poly-L-lactic acid, wherein the one or more *Enterococcus mundtii* strains have a negative saccharide utilization pattern for L-Xylose.

6. The method according to claim 5, wherein the one or more *Enterococcus mundtii* strains is *Enterococcus mundtii* NITE BP-965.

7. The method according to claim 1, wherein the one or more *Enterococcus mundtii* strains have a negative saccharide utilization pattern for Melezitose.

8. The method according to claim 5, wherein the one or more *Enterococcus mundtii* strains have a negative saccharide utilization pattern for Melezitose.

9. The method according to claim 5, wherein the medium comprises one or more cellooligosaccharides as a substrate, and the cellooligosaccharides are cellotriose and cellotetraose.

* * * * *